United States Patent
Yokoyama et al.

(10) Patent No.: US 11,056,653 B2
(45) Date of Patent: Jul. 6, 2021

(54) ORGANIC ELECTROLUMINESCENCE DEVICE

(71) Applicant: HODOGAYA CHEMICAL CO., LTD., Tokyo (JP)

(72) Inventors: Norimasa Yokoyama, Tokyo (JP); Shuichi Hayashi, Tokyo (JP); Naoaki Kabasawa, Tokyo (JP); Takeshi Yamamoto, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 334 days.

(21) Appl. No.: 16/094,695

(22) PCT Filed: Apr. 18, 2017

(86) PCT No.: PCT/JP2017/015537
§ 371 (c)(1),
(2) Date: Oct. 18, 2018

(87) PCT Pub. No.: WO2017/183625
PCT Pub. Date: Oct. 26, 2017

(65) Prior Publication Data
US 2020/0328353 A1    Oct. 15, 2020

(30) Foreign Application Priority Data

Apr. 22, 2016   (JP) .............. JP2016-086422

(51) Int. Cl.
*H01L 51/00*   (2006.01)
*H01L 51/50*   (2006.01)
*H01L 51/52*   (2006.01)

(52) U.S. Cl.
CPC ...... *H01L 51/0069* (2013.01); *H01L 51/0059* (2013.01); *H01L 51/0067* (2013.01);
(Continued)

(58) Field of Classification Search
CPC ............. H01L 51/0069; H01L 51/0059; H01L 51/0067; H01L 51/0061; H01L 51/0071; H01L 51/0072
See application file for complete search history.

(56) References Cited

U.S. PATENT DOCUMENTS

2008/0023724 A1   1/2008   Takeda et al.
2012/0138918 A1   6/2012   Naraoka et al.
(Continued)

FOREIGN PATENT DOCUMENTS

JP   1996-H08-048656 A   2/1996
JP          3194657 B2    6/2001
(Continued)

OTHER PUBLICATIONS

Machine Translation of WO 2015/001726.*
(Continued)

*Primary Examiner* — Anthony Ho
(74) *Attorney, Agent, or Firm* — Saliwanchik, Lloyd & Eisenschenk

(57) ABSTRACT

Object
To provide an organic electroluminescence device including, in order to improve the device characteristics of the organic electroluminescence device, particularly, to absorb light having the wavelengths of from 400 nm to 410 nm from sunlight, not to affect a material inside the device, and to significantly improve the light extraction efficiency, a capping layer formed of a material that has a high absorption coefficient, a high refractive index, and an excellent stability, durability, and light resistance of a thin film, and does not absorb light in the blue, green, and red wavelength range.
Solving Means
An organic electroluminescence device including at least an anode electrode, a hole transport layer, a light emitting layer, an electron transport layer, a cathode electrode, and a
(Continued)

capping layer in the stated order, in which the capping layer includes a material having an extinction coefficient of not less than 0.3 at wavelengths of from 400 nm to 410 nm and an absorbance of not less than 0.2 at wavelengths of from 400 nm to 410 nm in an absorption spectrum of a concentration of $10^{-5}$ mol/l.

15 Claims, 1 Drawing Sheet

(52) U.S. Cl.
CPC ...... *H01L 51/5056* (2013.01); *H01L 51/5072* (2013.01); *H01L 51/5206* (2013.01); *H01L 51/5221* (2013.01)

(56) References Cited

U.S. PATENT DOCUMENTS

| | | |
|---|---|---|
| 2014/0225100 A1 | 8/2014 | Yokoyama et al. |
| 2017/0186967 A1 | 6/2017 | Hayashi et al. |

FOREIGN PATENT DOCUMENTS

| | | |
|---|---|---|
| JP | 2006-302878 A | 11/2006 |
| WO | WO-2011/043083 A1 | 4/2011 |
| WO | WO-2013/038627 A1 | 3/2013 |
| WO | WO-2015/001726 A1 | 1/2015 |
| WO | WO-2015/190400 A1 | 12/2015 |

OTHER PUBLICATIONS

International Search Report in International Application No. PCT/JP2017/015537, filed Apr. 18, 2017.
Hosokawa, C. etal., "Development of Styryl-Based Light Emitting Material," *The Japan Society of Applied Physics 9th Lecture Preprints*, 2001, pp. 55-61, with its English Translation.
Hung, L. S. et al., "Application of an ultrathin LiF/Al bilayer in organic surface-emitting diodes," *Applied Physics Letters*, Jan. 22, 2001, 78(4):544-546, American Institute of Physics.
Riel, H. et al., "Phosphorescent top-emitting organic light-emitting devices with improved light outcoupling," *Applied Physics Letters*, Jan. 20, 2003, 82(3):466-468, American Institute of Physics.
Dyall, L. K. etal., "Oxidative Cyclizations. VIII* Mechanisms of Oxidation of ortho-Substituted Benzenamines and Improved Cyclizations by Bis(acetato-O)phenyliodine," Aust. J. Chem., 1992, 45:371-384.
Ishiyama, T. et al., "Palladium(0)-Catalyzed Cross-Coupling Reaction of Alkoxydiboron with Haloarenes: A Direct Procedure for Arylboronic Esters," *J. Org. Chem.*, 1995, 60:7508-7510, American Chemical Society.
Miyaura, N. et al., "The Palladium-Catalyzed Cross-Coupling Reaction of Phenylboronic Acid with Haloarenes in the Presence of Bases," *Synthetic Communications*, 1981, 11(7):513-519, Marcel Dekker, Inc.
Endo, A. et al., "Efficient up-conversion of triplet excitons into a singlet state and its application for organic light emitting diodes," *Applied Physics Letters*, 2011, 95:1-3, American Institute of Physics.
Chinese Office Action dated Jun. 30, 2020 in Chinese Application No. 201780021933.0, along with its English translation.
Supplementary European Search Report dated Oct. 28, 2019 in European Application No. 17785963.4.
Office Action dated May 26, 2020 in Japanese Application No. 2018-513181, along with its English translation.
Office Action dated Sep. 8, 2020 in Japanese Application No. 2018-513181, along with its English translation.
Office Action dated Dec. 14, 2020 in Chinese Application No. 201780021933.0, along with its English translation.
Office Action dated Mar. 8, 2021 in Chinese Application No. 201780021933.0, along with its English translation.
Office Action dated Feb. 28, 2021 in Korean Application No. 10-2018-7025474, along with its English translation.

* cited by examiner

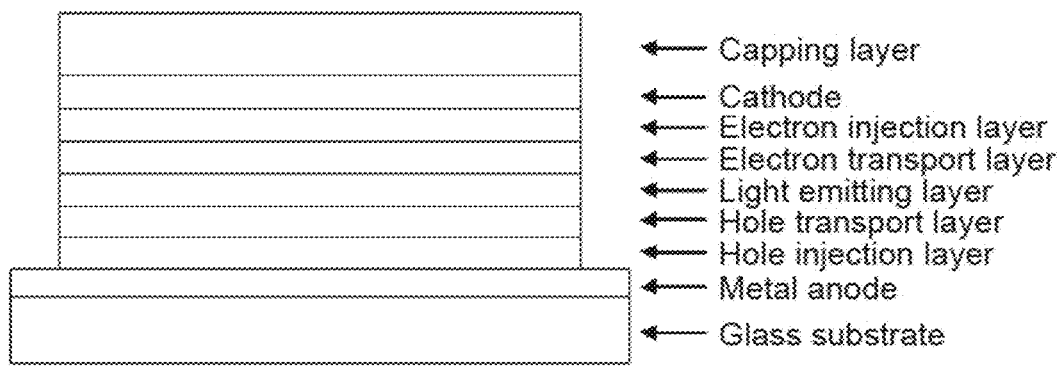

ORGANIC ELECTROLUMINESCENCE DEVICE

CROSS-REFERENCE TO RELATED APPLICATIONS

This application is the U.S. national stage application of International Patent Application No. PCT/JP2017/015537, filed Apr. 18, 2017, which claims the benefit under 35 U.S.C. § 119 of Japanese Application No. 2016-086422, filed Apr. 22, 2016, the disclosures of each of which are incorporated herein by reference in their entirety.

TECHNICAL FIELD

The present invention relates to an organic electroluminescence device (hereinafter, abbreviated as "organic EL device") that is a self-light emitting device suitable for various display apparatuses. Specifically, the present invention relates to an organic EL device using a specific arylamine compound, and particularly to an organic EL device having significantly improved light resistance.

BACKGROUND ART

Since the organic EL device is a self-light emitting device, it is brighter than the liquid crystal device and excellent in visibility, and capable of performing clear display. For that reason, active research has been done.

In 1987, C. W. Tang et al. (Eastman Kodak Company) have developed a stacked structural device in which various roles are assigned to the materials, thereby putting an organic EL device using an organic material to practical use. They have achieved high luminance of not less than 1000 $cd/m^2$ with voltage of not more than 10 V by stacking a phosphor capable of transporting electrons and an organic material capable of transporting holes and injecting both charges into a phosphor layer to emit light (see Patent Literature 1 and Patent Literature 2).

Many improvements have been made for practical use of the organic EL device until now. In an electroluminescence element that subdivides the various roles in the stacked structure and includes an anode, a hole injection layer, a hole transport layer, a light emitting layer, an electron transport layer, an electron injection layer, and a cathode in the stated order on a substrate, a high efficiency and durability have been achieved with a light emitting device having a bottom emission structure in which light is emitted from the bottom (see, for example, Non Patent Literature 1).

In recent years, a light emitting device having a top emission structure in which a metal having a high work function is used as an anode and light is emitted from the top is being used. Unlike the light emitting device having a bottom emission structure in which the area of a light emitting unit is limited by a pixel circuit, the light emitting device having a top-emission structure has an advantage that the area of the light emitting unit can be increased. In the light emitting device having a top-emission structure, a semi-transparent electrode, e.g., LiF/Al/Ag (see, for example, Non-Patent Literature 2), Ca/Mg (see, for example, Non-Patent Literature 3), or LiF/MgAg, is used as a cathode.

In such a light emitting device, when light emitted from the light emitting layer enters a different film at a certain angle or more, the light is totally reflected at the interface between the light emitting layer and the different film. For that reason, only a part of the emitted light has been available. In recent years, in order to improve the light extraction efficiency, a light emitting device including a "capping layer" having a high refractive index outside a semi-transparent electrode having a low refractive index has been proposed (see, for example, Non-Patent Literatures 2 and 3).

Regarding the effect of the capping layer in the light emitting device having a top-emission structure, in the light emitting device using $Ir(ppy)_3$ as a light emitting material, the current efficiency is 38 cd/A in the case that there is no capping layer. Meanwhile, in the light emitting device using ZnSe having a film thickness of 60 nm as a capping layer, the current efficiency is 64 cd/A, and thus, improvement in efficiency of approximately 1.7 times has been confirmed. Further, it has been shown that the maximum point of the transmittance and the maximum point of the efficiency between the semi-transparent electrode and the capping layer do not necessarily correspond to each other, and the maximum point of the light extraction efficiency is determined by the interference effect (see, for example, Non-Patent Literature 3).

It has been proposed to use a metal mask having high precision for forming a capping layer. However, such metal mask has a problem that alignment accuracy is deteriorated by distortion due to heat. That is, since ZnSe has a melting point as high as not less than 1100° C. (see, for example, Non-Patent Literature 3), it is not possible to perform deposition at an accurate position with a metal mask having high precision. Many inorganic materials have a high deposition temperature and are not suitable for use with a mask having high precision, which may damage the light emitting device itself. Further, in film formation by a sputtering method, since the light emitting device is damaged, a capping layer using an inorganic material as a constituent material cannot be used.

In the case of using tris (8-hydroxyquinoline) aluminum (hereinafter, abbreviated as $Alq_3$) as a capping layer for adjusting a refractive index (see, for example, Non-Patent Literature 2), $Alq_3$ slightly absorbs light at 450 nm used for a blue light emitting device although it is known as an organic EL material generally used as a green light emitting material or electron transport material. For that reason, in the case of a blue light emitting device, there has been a problem that both the color purity and the light extraction efficiency are reduced.

Further, a device prepared by an existing capping layer has a problem that light having the wavelength of from 400 nm to 410 nm from sunlight is transmitted therethrough, which affects a material inside the device, and both the color purity and the light extraction efficiency are reduced.

In order to improve the device characteristics of the organic electroluminescence device, particularly, to absorb light having the wavelengths of from 400 nm to 410 nm from sunlight, not to affect a material inside the device, and to significantly improve the light extraction efficiency, a material that has a high absorption coefficient, a high refractive index, and an excellent stability, durability, and light resistance of a thin film is desired as a material of the capping layer.

CITATION LIST

Patent Literature

Patent Literature 1: Japanese Patent Application Laid-open No. 1996-048656
Patent Literature 2: Japanese Patent No. 3194657
Patent Literature 3: WO 2013-038627

Non-Patent Literature

Non-Patent Literature 1: The Japan Society of Applied Physics 9th Lecture Preprints pp. 55 to 61 (2001)
Non-Patent Literature 2: Appl. Phys. Lett., 78, 544 (2001)
Non-Patent Literature 3: Appl. Phys. Lett., 82, 466 (2003)
Non-Patent Literature 4: Aust. J. Chem., 45, 371 (1992)
Non-Patent Literature 5: J. Org. Chem., 60, 7508 (1995)
Non-Patent Literature 6: Synth. Commun., 11, 513 (1981)
Non-Patent Literature 7: Appl. Phys. Let., 98, 083302 (2011)

DISCLOSURE OF INVENTION

Technical Problem

It is an object of the present invention to provide an organic EL device including, in order to improve the device characteristics of the EL device, particularly, to absorb light having the wavelengths of from 400 nm to 410 nm from sunlight, not to affect a material inside the device, and to significantly improve the light extraction efficiency, a capping layer formed of a material that has a high absorption coefficient, a high refractive index, and an excellent stability, durability, and light resistance of a thin film, and does not absorb light in the blue, green, and red wavelength range.

Examples of physical characteristics of the material of the capping layer suitable for the present invention include (1) having a high absorption coefficient, (2) having a high refractive index, (3) being able to be deposited and not thermally decomposed, (4) being stable in a thin-film state, and (5) having a high glass transition temperature. Further, examples of physical characteristics of the device suitable for the present invention include (1) absorbing light having the wavelengths of from 400 nm to 410 nm, (2) having high light extraction efficiency, (3) having no reduction in color purity, (4) causing light to be transmitted therethrough without changing over time, and (5) having a long life span.

Solution to Problem

In order to achieve the above-mentioned object, the present inventors have focused on the fact that an arylamine-based material has an excellent stability and durability of a thin-film, selected a specific arylamine compound having a high refractive index and a material having high absorbance at wavelengths of from 400 nm to 410 nm in an absorption spectrum of a concentration of $10^{-5}$ mol/l, prepared an organic EL device using it as a material forming the capping layer, and intensively evaluated the characteristics of the device, thereby completing the present invention.

That is, according to the present invention, the following organic EL device is provided.

1) An organic electroluminescence device including: at least an anode electrode; a hole transport layer; a light emitting layer; an electron transport layer; a cathode electrode; and a capping layer in the stated order, wherein the capping layer includes a material having an extinction coefficient of not less than 0.3 at wavelengths of from 400 nm to 410 nm and an absorbance of not less than 0.2 at wavelengths of from 400 nm to 410 nm in the absorption spectrum of a concentration of $10^{-5}$ mol/l.

2) The organic electroluminescence device according to 1) above, in which the material of the capping layer has an extinction coefficient of not less than 0.1 at wavelengths of from 410 nm to 430 nm.

3) The organic electroluminescence device according to 1) above, in which the capping layer includes an arylamine compound represented by a following general formula (1).

[Chem. 1]

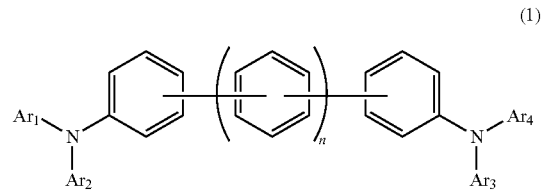

(1)

(in the formula, $Ar_1$, $Ar_2$, $Ar_3$, and $Ar_4$ may be the same or different from each other and each represent a substituted or unsubstituted aromatic hydrocarbon group, a substituted or unsubstituted aromatic heterocyclic group, or a substituted or unsubstituted condensed polycyclic aromatic group. n represents an integer of 0 to 4. Here, at least one of $Ar_1$, $Ar_2$, $Ar_3$, and $Ar_4$ is a monovalent group represented by a following structural formula (B) or has the monovalent group as a substituent.)

[Chem. 2]

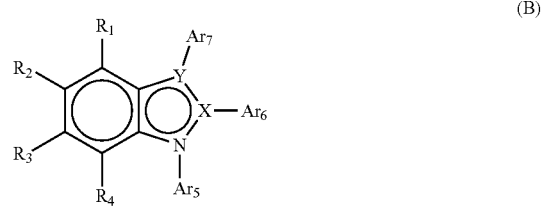

(B)

(in the formula, $R_1$, $R_2$, $R_3$, and $R_4$ may be the same or different from each other, be a linking group, a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_1$, $R_2$, $R_3$, and $R_4$ may be bonded to each other to form a ring via a single bond, a substituted or unsubstituted methylene group, an oxygen atom, a sulfur atom, or N—$Ar_8$. $Ar_8$ represents a substituted or unsubstituted aromatic hydrocarbon group, a substituted or unsubstituted aromatic heterocyclic group, or a substituted or unsubstituted condensed polycyclic aromatic group. X represents a carbon atom or a nitrogen atom. Y represents a carbon atom, an oxygen atom, a sulfur atom, or a nitrogen atom. $Ar_5$ represents a linking group, a substituted or unsubstituted aromatic hydrocarbon group, a substituted or unsubstituted aromatic heterocyclic group, or a substituted or unsubstituted condensed polycyclic aromatic group. $Ar_6$ and $Ar_7$ may be the same or different from each other, be a linking group, a substituted or unsubstituted aromatic hydrocarbon group, a substituted or unsubstituted aromatic heterocyclic group, or a substituted or unsubstituted condensed polycyclic aromatic group. Y does not have $Ar_7$ in the case that Y is an oxygen atom or a sulfur atom. Any one of $Ar_5$, $Ar_6$, and $Ar_7$ is a linking group or a substituent in the case that X and Y are each a nitrogen atom. X does not have $Ar_6$ in the case that X is a nitrogen atom and Y is a carbon atom. $Ar_8$ represents a substituted or unsubstituted aromatic hydrocarbon group, a substituted or unsubstituted aromatic heterocyclic group, or a substituted or unsubstituted condensed polycyclic aromatic group. However, only one of $R_1$, $R_2$, $R_3$, $R_4$, $Ar_5$, $Ar_6$, and $Ar_7$ is a linking group, and a case that X is a nitrogen atom and Y is an oxygen atom or sulfur atom is excluded.)

4) The organic electroluminescence device according to 1) above, in which the structural formula (B) is a monovalent group represented by a following structural formula (B-1).

[Chem. 3]

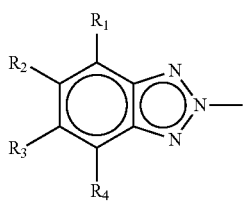

(B-1)

(in the formula, $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_1$, $R_2$, $R_3$, and $R_4$ may be bonded to each other to form a ring via a single bond, a substituted or unsubstituted methylene group, an oxygen atom, a sulfur atom, or N—$Ar_8$. $Ar_8$ represents a substituted or unsubstituted aromatic hydrocarbon group, a substituted or unsubstituted aromatic heterocyclic group, or a substituted or unsubstituted condensed polycyclic aromatic group.)

5) The organic electroluminescence device according to 1) above, in which the structural formula (B) is a monovalent group represented by a following structural formula (B-2).

[Chem. 4]

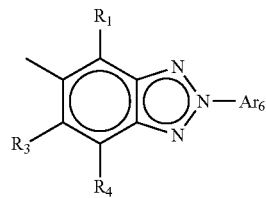

(B-2)

(B-2)
(in the formula, $R_1$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_3$ and $R_4$ may be bonded to each other to form a ring via a single bond, a substituted or unsubstituted methylene group, an oxygen atom, a sulfur atom, or N—$Ar_8$. $Ar_6$ and $Ar_8$ may be the same or different from each other and each represent a substituted or unsubstituted aromatic hydrocarbon group, a substituted or unsubstituted aromatic heterocyclic group, or a substituted or unsubstituted condensed polycyclic aromatic group.)

6) The organic electroluminescence device according to 1) above, in which the structural formula (B) is a monovalent group represented by a following structural formula (B-3).

[Chem. 5]

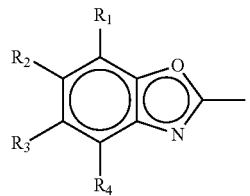

(B-3)

(in the formula, $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_1$, $R_2$, $R_3$, and $R_4$ may be bonded to each other to form a ring via a single bond, a substituted or unsubstituted methylene group, an oxygen atom, a sulfur atom, or N—$Ar_8$. $Ar_8$ represents a substituted or unsubstituted aromatic hydrocarbon group, a substituted or unsubstituted aromatic heterocyclic group, or a substituted or unsubstituted condensed polycyclic aromatic group.)

7) The organic electroluminescence device according to 1) above, in which the structural formula (B) is a monovalent group represented by a following structural formula (B-4).

[Chem. 6]

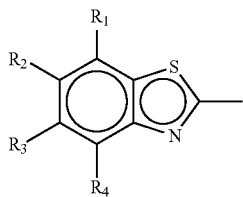

(B-4)

(in the formula, $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group. $R_1$, $R_2$, $R_3$, and $R_4$ may be bonded to each other to form a ring via a single bond, a substituted or unsubstituted methylene group, an oxygen atom, a sulfur atom, or N—$Ar_8$. $Ar_8$ represents a substituted or unsubstituted aromatic hydrocarbon group, a substituted or unsubstituted aromatic heterocyclic group, or a substituted or unsubstituted condensed polycyclic aromatic group.)

8) The organic electroluminescence device according to 1) above, in which the structural formula (B) is a monovalent group represented by a following structural formula (B').

[Chem. 7]

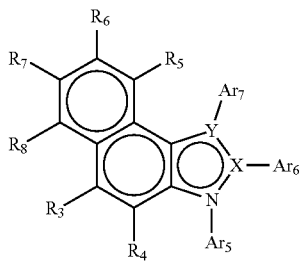

(B')

(in the formula, $R_3$, $R_4$, $R_5$, $R_6$, $R_7$, and $R_8$ may be the same or different from each other, be a linking group, a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group $R_3$, $R_4$, $R_5$, $R_6$, $R_7$, and $R_8$ may be bonded to each other to form a ring via a single bond, a substituted or unsubstituted methylene group, an oxygen atom, a sulfur atom, or N—$Ar_8$. X represents a carbon atom or a nitrogen atom. Y represents a carbon atom, an oxygen atom, a sulfur atom, or a nitrogen atom. $Ar_5$ represents a linking group, a substituted or unsubstituted aromatic hydrocarbon group, a substituted or unsubstituted aromatic heterocyclic group, or a substituted or unsubstituted condensed polycyclic aromatic group. $Ar_6$ and $Ar_7$ may be the same or different from each other and each represent a linking group, a substituted or unsubstituted aromatic hydrocarbon group, a substituted or unsubstituted aromatic heterocyclic group, or a substituted or unsubstituted condensed polycyclic aromatic group. Y does not have $Ar_7$ in the case that Y is an oxygen atom or a sulfur atom. Any one of $Ar_5$, $Ar_6$, and $Ar_7$ is a linking group or a substituent in the case that X and Y are each a nitrogen atom. X does not have $Ar_6$ in the case that X is a nitrogen atom and Y is a carbon atom. $Ar_8$ represents a substituted or unsubstituted aromatic hydrocarbon group, a substituted or unsubstituted aromatic heterocyclic group, or a substituted or unsubstituted condensed polycyclic aromatic group. However, only one of $R_3$, $R_4$, $R_5$, $R_6$, $R_7$, $R_8$, $Ar_5$, $Ar_6$, and $Ar_7$ is a linking group, and a case that X is a nitrogen atom and Y is an oxygen atom or sulfur atom is excluded.)

9) The organic electroluminescence device according to 1) above, in which n is 0 in the general formula (1).

10) The organic electroluminescence device according to 1) above, in which n is 1 in the general formula (1).

11) The organic electroluminescence device according to 1) above, in which n is 2 in the general formula (1).

12) The organic electroluminescence device according to 1) above, in which any two of $Ar_1$, $Ar_2$, $Ar_3$, and $Ar_4$ are each a monovalent group represented by the structural formula (B) or each have the monovalent group as a substituent in the general formula (1).

13) The organic electroluminescence device according to 1) above, in which $Ar_1$ and $Ar_4$ are each a monovalent group represented by the structural formula (B) or each have the monovalent group as a substituent in the general formula (1).

14) The organic electroluminescence device according to 1) above, in which the capping layer has a thickness in the range of 30 nm to 120 nm.

15) The organic electroluminescence device according to 1) above, in which the capping layer has a refractive index of not less than 1.85 in the wavelength range of from 400 nm to 750 nm of light transmitted through the capping layer.

16) A method of using a compound represented by the general formula (1) as a capping layer of an organic electroluminescence device.

Examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the general formula (1) include, specifically, a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group, a triphenylenyl group, a pyridyl group, a furil group, a pyrrolyl group, a thienyl group, a quinolyl group, an isoquinolyl group, a benzofuranyl group, a benzothienyl group, an indolyl group, a carbazolyl group, a benzotriazolyl group, a benzoxazolyl group, a benzothiazolyl group, a quinoxalyl group, a benzimidazolyl group, a pyrazolyl group, a dibenzofuranyl group, a dibenzothienyl group, and a carbolinyl group. Further, $Ar_1$ and $Ar_2$, or $Ar_3$ and $Ar_4$ may be bonded to each other to form a ring via a single bond, a substituted or unsubstituted methylene group, an oxygen atom, a sulfur atom, or N—$Ar_8$. Here, "N" in "N—$Ar_8$" represents a nitrogen atom, "$Ar_8$" is a "substituted or unsubstituted aromatic hydrocarbon group", "substituted or unsubstituted aromatic heterocyclic group", or "substituted or unsubstituted condensed polycyclic aromatic group", examples thereof include groups similar to those exemplified above, and similarly, also examples of the substituent that these groups may have include substituents exemplified below.

Examples of the substituent in the "substituted aromatic hydrocarbon group", "substituted aromatic heterocyclic group", or "substituted condensed polycyclic aromatic group" represented by $Ar_1$ to $Ar_4$ in the general formula (1) include, specifically, a deuterium atom, a trifluoromethyl group, a cyano group, a nitro group; halogen atoms such as a fluorine atom, a chlorine atom, a bromine atom, and an iodine atom; a linear or branched alkyl group having 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; a linear or branched alkyloxy group having 1 to 6 carbon atoms such as a methyloxy group, an ethyloxy group, and a propyloxy group; an alkenyl group such as an allyl group; an aralkyl group such as a benzyl group, a naphthylmethyl group, and a phenethyl group; an aryloxy group such as a phenyloxy group and a tolyloxy group; an arylalkyloxy group such as a benzyloxy group and a phenethyloxy group; an aromatic hydrocarbon group or condensed polycyclic aromatic group such as a phenyl group, a biphenylyl group, a terphenylyl group, a naphthyl group, an anthracenyl group, a phenanthryl group, a fluorenyl group, an indenyl group, a pyrenyl group, a perylenyl group, a fluoranthenyl group, and a triphenylenyl group; an aromatic heterocyclic group such as a pyridyl group, a furil group, a thienyl group, a pyrrolyl group, a quinolyl group, an isoquinolyl group, a benzofuranyl group, a benzothienyl group, an indolyl group, a carbazolyl group, a benzotriazolyl group, a benzoxazolyl group, a benzothiazolyl group, a quinoxalyl group, a benzimidazolyl group, a pyrazolyl group, a dibenzofuranyl group, a dibenzothienyl group, and a carbolinyl group; an arylvinyl group such as a styryl group and a naphthylvinyl group; an acyl group such as an acetyl group and a benzoyl group; a dialkylamino group such as a dimethylamino group and a diethylamino group; a disubstituted amino group substituted with an aromatic hydrocarbon group or a condensed polycyclic aromatic group such as a diphenylamino group and a dinaphthylamino group; a diaralkylamino group such as a dibenzylamino group and a diphenethylamino group; a disubstituted amino group substituted with an aromatic heterocyclic group such as a dipyridylamino group and a dithienylamino group; a dialkenylamino group such as a diallylamino group; and groups such as a disubstituted amino group substituted with a substituent selected from an alkyl group, an aromatic hydrocarbon group, a condensed polycyclic aromatic group, an aralkyl group, an aromatic heterocyclic group, and an alkenyl group, and these substituents may be further substituted with the substituents exemplified above.

Further, these substituents may be bonded to each other to form a ring via a single bond, a substituted or unsubstituted methylene group, an oxygen atom, a sulfur atom, or N—$Ar_8$. Here, "N—$Ar_8$" means the same one as that defined regarding the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1).

Examples of the "linear or branched alkyl group having 1 to 6 carbon atoms", "cycloalkyl group having 5 to 10 carbon atoms", or "linear or branched alkenyl group having 2 to 6 carbon atoms" in the "linear or branched alkyl group having 1 to 6 carbon atoms, which may have a substituent", "cycloalkyl group having 5 to 10 carbon atoms, which may have a substituent", or "linear or branched alkenyl group having 2 to 6 carbon atoms, which may have a substituent" represented by $R_1$ to $R_8$ in the structural formulae (B), (B-1), (B-2), (B-3), (B-4), and (B') include, specifically, a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-buthenyl group, and these groups may be bonded to each other to form a ring via a single bond, a substituted or unsubstituted methylene group, an oxygen atom, a sulfur atom, or N—$Ar_8$. Here, "N—$Ar_8$" means the same one as that defined regarding the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1).

Examples of the "substituent" in the "linear or branched alkyl group having 1 to 6 carbon atoms, which has a substituent", "cycloalkyl group having 5 to 10 carbon atoms, which has a substituent", or "linear or branched alkenyl group having 2 to 6 carbon atoms, which has as substituent" represented by $R_1$ to $R_8$ in the structural formulae (B), (B-1), (B-2), (B-3), (B-4), and (B') include the same one as that shown regarding the "substituent" in the "substituted aromatic hydrocarbon group", "substituted aromatic heterocyclic group", or "substituted condensed polycyclic aromatic group" represented by $Ar_1$ to $Ar_4$ in the above-mentioned general formula (1), and also possible forms thereof are similar thereto.

Examples of the "linear or branched alkyloxy group having 1 to 6 carbon atoms" or "cycloalkyloxy group having 5 to 10 carbon atoms" in the "linear or branched alkyloxy group having 1 to 6 carbon atoms, which may have a substituent" or "cycloalkyloxy group having 5 to 10 carbon atoms, which may have a substituent" represented by $R_1$ to $R_8$ In the structural formulae (B), (B-1), (B-2), (B-3), (B-4), and (B') include, specifically, a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, and these groups may be bonded to each other to form a ring via a single bond, a substituted or unsubstituted methylene group, an oxygen atom, a sulfur atom, or N—$Ar_8$. Here, "N—$Ar_8$" means the same one as that defined regarding the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1).

Examples of the "substituent" in the "linear or branched alkyloxy group having 1 to 6 carbon atoms, which has a substituent" or "cycloalkyloxy group having 5 to 10 carbon atoms, which has a substituent" represented by $R_1$ to $R_8$ in the structural formulae (B), (B-1), (B-2), (B-3), (B-4), and (B') include the same one as that shown regarding the "substituent" in the "substituted aromatic hydrocarbon group", "substituted aromatic heterocyclic group", or "substituted condensed polycyclic aromatic group" represented by $Ar_1$ to $Ar_4$ in the above-mentioned general formula (1), and also possible forms thereof are similar thereto.

Examples of the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $R_1$ to $R_8$ in the structural formulae (B), (B-1), (B-2), (B-3), (B-4), and (B') include the same one as that shown regarding the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1), and also possible forms thereof are similar thereto.

Examples of the "substituent" in the "substituted aromatic hydrocarbon group", "substituted aromatic heterocyclic group", or "substituted condensed polycyclic aromatic group" represented by $R_1$ to $R_8$ in the structural formulae (B), (B-1), (B-2), (B-3), (B-4), and (B') include the same one as that shown regarding the "substituent" in the "substituted aromatic hydrocarbon group", "substituted aromatic heterocyclic group", or "substituted condensed polycyclic aromatic group" represented by $Ar_1$ to $Ar_4$ in the above-mentioned general formula (1), and also possible forms thereof are similar thereto.

Examples of the "aryloxy group" in the "substituted or unsubstituted aryloxy group" represented by $R_1$ to $R_8$ in the structural formulae (B), (B-1), (B-2), (B-3), (B-4), and (B') include, specifically, a phenyloxy group, a tolyloxy group, a biphenylyloxy group, a terphenylyloxy group, a naphthyloxy group, an anthryloxy group, a phenanthryloxy group, a fluorenyloxy group, an indenyloxy group, a pyrenyloxy group, and a perylenyloxy group, and these groups may be bonded to each other to form a ring via/a single bond, a substituted or unsubstituted methylene group, an oxygen atom, a sulfur atom, or N—$Ar_8$. Here, "N—$Ar_8$" means the same one as that defined regarding the "substituent" in the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1).

Examples of the "substituent" in the "substituted aryloxy group" represented by $R_1$ to $R_8$ in the structural formulae (B), (B-1), (B-2), (B-3), (B-4), and (B') include the same one as that shown regarding the "substituent" in the "substituted aromatic hydrocarbon group", "substituted aromatic heterocyclic group", or "substituted condensed polycyclic aromatic group" represented by $Ar_1$ to $Ar_4$ in the above-mentioned general formula (1), and also possible forms thereof are similar thereto.

Examples of $Ar_6$ in the structural formula (B-2) and the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_5$, $Ar_6$, and $Ar_7$ in the structural formulae (B) and (B') include the same one as that shown regarding the "aromatic hydrocarbon group", "aromatic heterocyclic group", or "condensed polycyclic aromatic group" in the "substituted or unsubstituted aromatic hydrocarbon group", "substituted or unsubstituted aromatic heterocyclic group", or "substituted or unsubstituted condensed polycyclic aromatic group" represented by $Ar_1$ to $Ar_4$ in the above-mentioned general formula (1), and also possible forms thereof are similar thereto.

Examples of the "substituent" in the "substituted aromatic hydrocarbon group", "substituted aromatic heterocyclic group", or "substituted condensed polycyclic aromatic group" represented by $Ar_6$ in the structural formula (B-2) and $Ar_5$, $Ar_6$, and $Ar_7$ in the structural formulae (B) and (B') include the same one as that shown regarding the "substituent" in the "substituted aromatic hydrocarbon group", "substituted aromatic heterocyclic group", or "substituted condensed polycyclic aromatic group" represented by $Ar_1$ to $Ar_4$ in the above-mentioned general formula (1), and also possible forms thereof are similar thereto.

In the general formula (1), n represents an integer of 0 to 4, and is favorably 0, 1, or 2, and more favorably, 0 or 1.

In the general formula (1), a form in which at least one of $Ar_1$, $Ar_2$, $Ar_3$, and $Ar_4$ is the above-mentioned structural formula (B), a form in which at least one of $Ar_1$, $Ar_2$, $Ar_3$, and $Ar_4$ has the structural formula (B) as the substituent thereof, or a form in which at least one of $Ar_1$, $Ar_2$, $Ar_3$, and $Ar_4$ is the above-mentioned structural formula (B) and at least one of $Ar_1$, $Ar_2$, $Ar_3$, and $Ar_4$ includes the above-mentioned structural formula (B) as the substituent thereof are provided; a form in which any two of $Ar_1$, $Ar_2$, $Ar_3$, and $Ar_4$ are each the above-mentioned structural formula (B), a form in which any two of $Ar_1$, $Ar_2$, $Ar_3$, and $Ar_4$ each have the above-mentioned structural formula (B) as the substituent thereof, or a form in which any one of $Ar_1$, $Ar_2$, $Ar_3$, and $Ar_4$ is the above-mentioned structural formula (B) and any one of $Ar_1$, $Ar_2$, $Ar_3$, and $Ar_4$, which is not the above-mentioned structural formula (B), has the above-mentioned structural formula (B) as the substituent thereof is favorable; a form in which $Ar_1$ and $Ar_4$ are each the above-mentioned structural formula (B), a form in which $Ar_1$ and $Ar_4$ each have the above-mentioned structural formula (B) as the substituent thereof, or a form in which $Ar_1$ is the above-mentioned structural formula (B) and $Ar_4$ has the above-mentioned structural formula (B) as the substituent thereof is more favorable; and a form in which $Ar_1$ and $Ar_4$ each have the structural formula (B-1), (B-3), or (B-4) as the substituent thereof, or are each the structural formula (B-2) is more favorable.

As each of $Ar_1$, $Ar_2$, $Ar_3$, and $Ar_4$ in the general formula (1), an aromatic hydrocarbon group, a condensed polycyclic aromatic group, the above-mentioned structural formula (B), a thienyl group, a benzothienyl group, a dibenzofuranyl group, or a dibenzothienyl group is favorable, a phenyl group, a biphenylyl group, a terphenylyl group, a naphthyl group, a phenanthryl group, a fluorenyl group, the above-mentioned structural formula (B), a thienyl group, a benzothienyl group, a dibenzofuranyl group, or a dibenzothienyl group is more favorable, and a phenyl group, a biphenylyl group, a fluorenyl group, the above-mentioned structural formula (B), a dibenzofuranyl group, or a dibenzothienyl group is particularly favorable.

As each of $Ar_6$ in the structural formula (B-2) and $Ar_5$, $Ar_6$, and $Ar_7$ in the structural formulae (B) and (B'), an aromatic hydrocarbon group, a condensed polycyclic aromatic group, a thienyl group, a benzothienyl group, a dibenzofuranyl group, or a dibenzothienyl group is favorable, and a phenyl group, a biphenylyl group, a terphenylyl group, a naphthyl group, a phenanthryl group, a fluorenyl group, a thienyl group, a benzothienyl group, a dibenzofuranyl group, or a dibenzothienyl group is more favorable.

In the general formula (1), only one of $R_1$, $R_2$, $R_3$, $R_4$, $Ar_5$, $Ar_6$, and $Ar_7$ is a linking group.

In the structural formulae (B) and (B'), X represents a carbon atom or a nitrogen atom, and Y represents a carbon atom, an oxygen atom, a sulfur atom, or a nitrogen atom. Here, Y does not have a linking group of $Ar_7$ or a substituent ($Ar_7$ does not exist) in the case that Y is an oxygen atom or a sulfur atom, any one of $Ar_5$, $Ar_6$, and $Ar_7$ is a linking group or a substituent (any two of $Ar_5$, $Ar_6$, and $Ar_7$ do not exist) in the case that X and Y are each a nitrogen atom, and any of $Ar_5$ and $Ar_6$ is a linking group or a substituent (any of $Ar_5$ and $Ar_6$ does not exist) in the case that X is a nitrogen atom and Y is a carbon atom.

In the structural formulae (B) and (B'), in the case that X is a nitrogen atom, Y is favorably a nitrogen atom. In this case, from the viewpoint of stability of the compound, it is favorable that a linking group of $Ar_5$, $Ar_6$, or $Ar_7$ bonds to a carbon atom of $Ar_1$, $Ar_2$, $Ar_3$, or $Ar_4$ (the structural formula (B) or (B') is a substituent of $Ar_1$, $Ar_2$, $Ar_3$, or $Ar_4$.

In the structural formula (B) and (B'), in the case that X is a carbon atom, Y is favorably a carbon atom, an oxygen atom, or a sulfur atom, and more favorably an oxygen atom or a sulfur atom.

In the structural formulae (B) and (B'), a case that X is a nitrogen atom and Y is an oxygen atom or a sulfur atom is excluded from the present invention.

In the organic EL device of the present invention, the extinction coefficient of the capping layer in the wavelength range of from 400 nm to 410 nm of light transmitted through the capping layer is favorably not less than 0.30, and more favorably not less than 0.40.

The arylamine compound represented by the above-mentioned general formula (1), which is suitably used in the organic EL device of the present invention, can be used as a constituent material of a hole injection layer, a hole transport layer, a light emitting layer, an electron blocking layer, or a capping layer of the organic EL device.

Further, in the organic EL device of the present invention, the thickness of the capping layer is favorably in the range of 30 nm to 120 nm, and more favorably in the range of 40 nm to 80 nm.

Further, in the organic EL device of the present invention, the refractive index of the capping layer in the wavelength range of 450 nm to 750 nm of light transmitted through the capping layer is favorably not less than 1.85, and more favorably not less than 1.90.

Further, in the organic EL device of the present invention, the capping layer may be prepared by stacking two or more different constituent materials.

Advantageous Effects of Invention

The organic EL device of the present invention includes a capping layer that is provided outside a transparent or semi-transparent electrode and has a refractive index higher than that of the semi-transparent electrode. Accordingly, it is possible to obtain the organic EL device capable of significantly improving the light extraction efficiency. Further, by using the arylamine compound represented by the general formula (1) for the capping layer, it is possible to perform deposition at the temperature of not more than 400° C. Therefore, it is possible to optimize the light extraction efficiency of each color using a mask having high precision without damaging the light emitting device, and display a clear and bright image with high color purity, which can be suitably applied to a full-color display.

In the organic EL device of the present invention, a material for the organic EL device, which has a high absorption coefficient and a high refractive index, and is excellent in stability, durability, and light resistance of a thin film, is used as the material of the capping layer. Accordingly, it is possible to maintain the color purity and significantly improve the light extraction efficiency without being affected by sunlight, as compared with the existing organic EL device. Further, it has become possible to realize the organic EL device with high efficiency and a long life span.

BRIEF DESCRIPTION OF DRAWINGS

FIG. 1 is a diagram showing a configuration of an organic EL device according to an example 10 and a comparative example 1.

MODE(S) FOR CARRYING OUT THE INVENTION

The arylamine compound represented by the above-mentioned general formula (1), which is suitable used for the organic EL device of the present invention is a novel compound, and these compounds can be synthesized as follows, for example. For example, by synthesizing a 2-aminoarylazobenzene derivative from a 1,2-diaminobenzene derivative and a nitroaryl derivative by a known method, and causing an oxidative cyclization reaction by bis(acetato-O) phenyliodine to occur, it is possible to synthesize a benzotriazole derivative having an aryl group (see, for example, Non-Patent Literature 4).

Here, by using a 1,2-diaminobenzene derivative or nitroaryl derivative having a halogen atom, e.g., a bromo atom as a substituent, it is possible to synthesize a bromo-substituted compound of a benzotriazole derivative having an aryl group. Subsequently, by causing a condensation reaction of this bromo-substituted compound and diarylamine by the Ullmann reaction, the Buchwald-Hartwig reaction, or the like to occur, it is possible to synthesize the arylamine compound represented by the general formula (1) of the present invention.

Further, also by brominating the synthesized benzotriazole derivative having an aryl group with an N-bromosuccinimide or the like, it is possible to synthesize a brominated benzotriazole derivative. Here, by changing the reagent and conditions of the bromination, it is possible to obtain bromo-substituted compounds with different substitution positions.

Then, by causing a similar reaction to occur, it is possible to synthesize the arylamine compound represented by the general formula (1) of the present invention.

Further, also by causing a cross coupling reaction (see, for example, Non-Patent Literature 6) such as Suzuki coupling of this bromo-substituted compound and a boronic acid or boronic acid ester derivative, which is synthesized by reaction of various aryl halides and a pinacolborane or bis(pinacolato) diboron (see, for example, Non-Patent Literature 5), to occur, it is possible to synthesize the arylamine compound represented by the general formula (1) of the present invention.

Further, also by synthesizing a boronic acid or boronic acid ester derivative (see, for example, Non-Patent Literature 5) from the bromo-substituted compound, and causing a cross coupling reaction (see, for example, Non-Patent Literature 6) such as Suzuki coupling with various aryl halides having a diarylamino group to occur, it is possible to synthesize the arylamine compound represented by the general formula (1) of the present invention.

Here, by causing a similar reaction of a bromo-substituted compound of a benzothiazole derivative, benzoxazole derivative, or indole derivative having a corresponding substituent or the brominated bromo-substituted compound to occur, it is possible to synthesize the arylamine compound represented by the general formula (1) of the present invention having a benzothiazole group, benzoxazole group, or indole group.

Examples of particularly favorable compounds among arylamine compounds represented by the general formula (1), which is suitably used for the organic EL device of the present invention are shown below. However, the present invention is not limited to these compounds.

[Chem. 8]

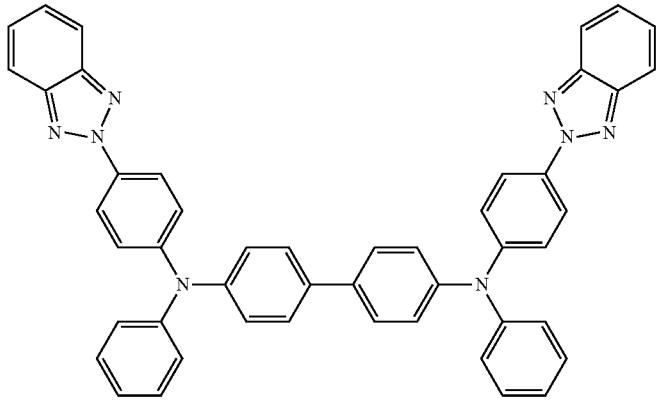

(1-1)

[Chem. 9]

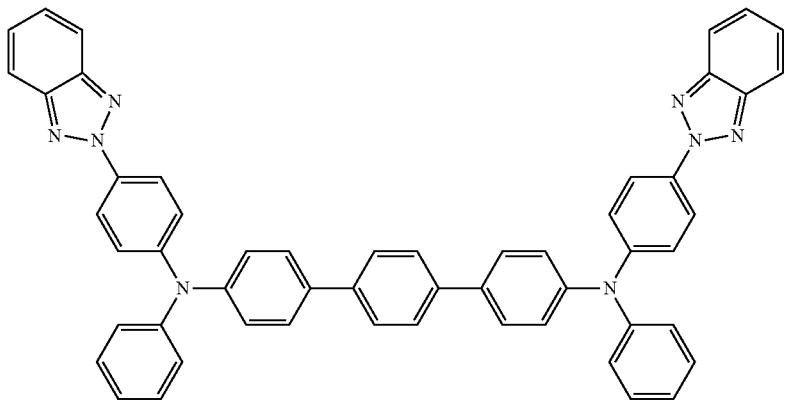

(1-2)

[Chem. 10]

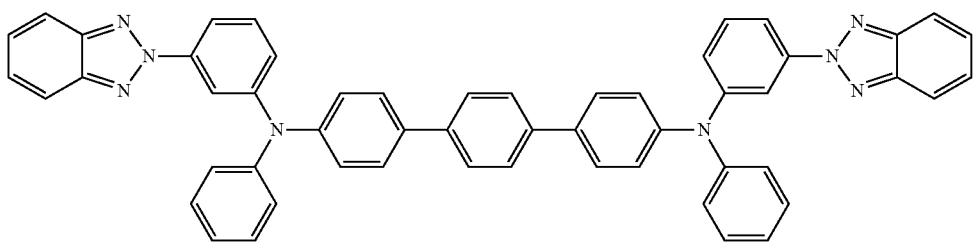

(1-3)

[Chem. 11]
(1-4)
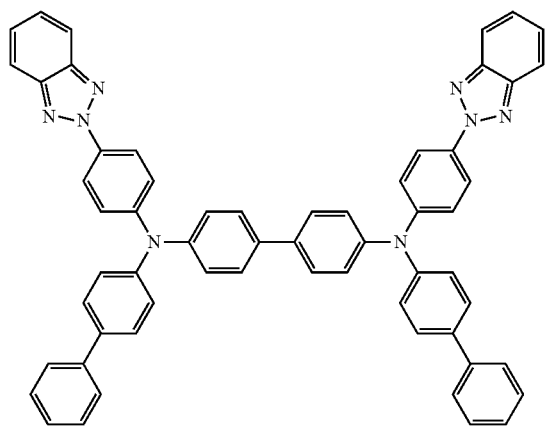
[Chem. 12]
(1-5)
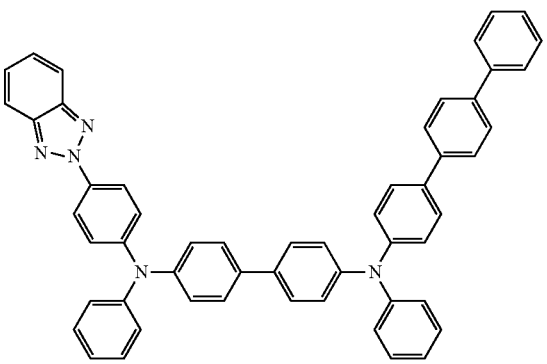
[Chem. 13]
(1-6)
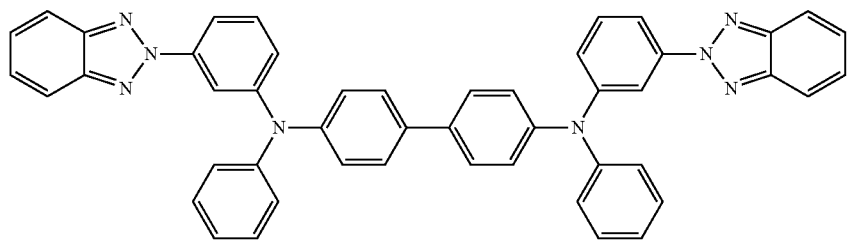
[Chem. 14]
(1-7)
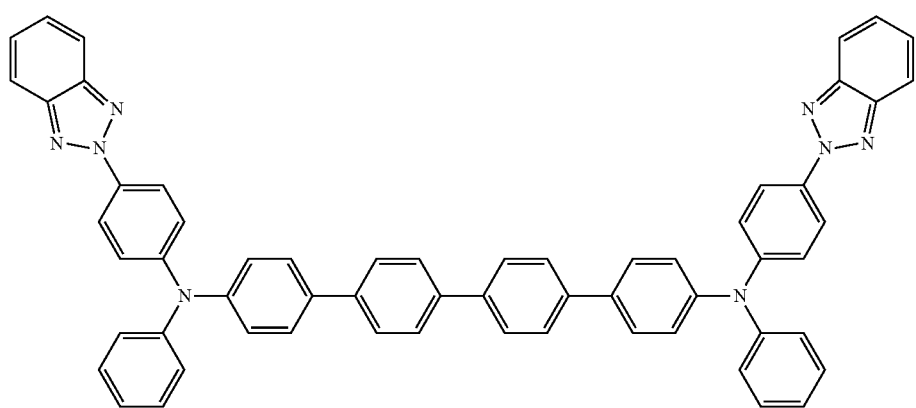

[Chem. 15]
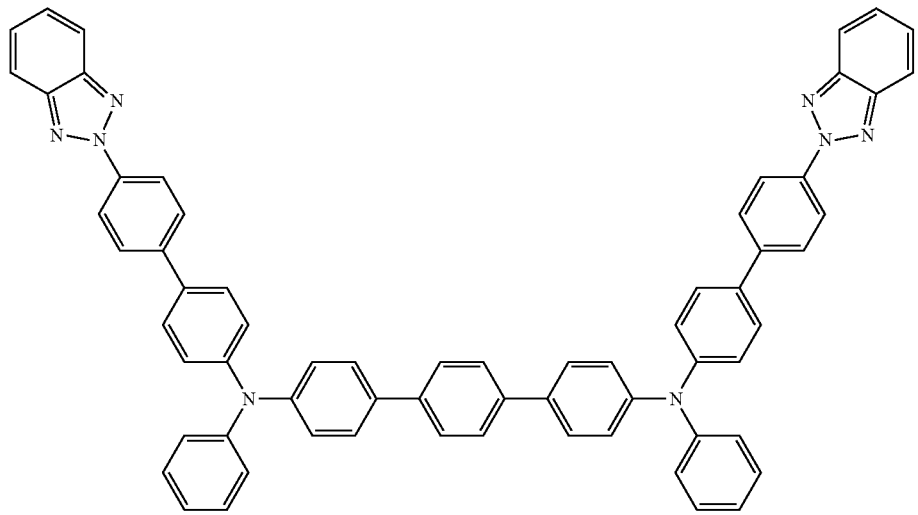
(1-8)
[Chem. 16]
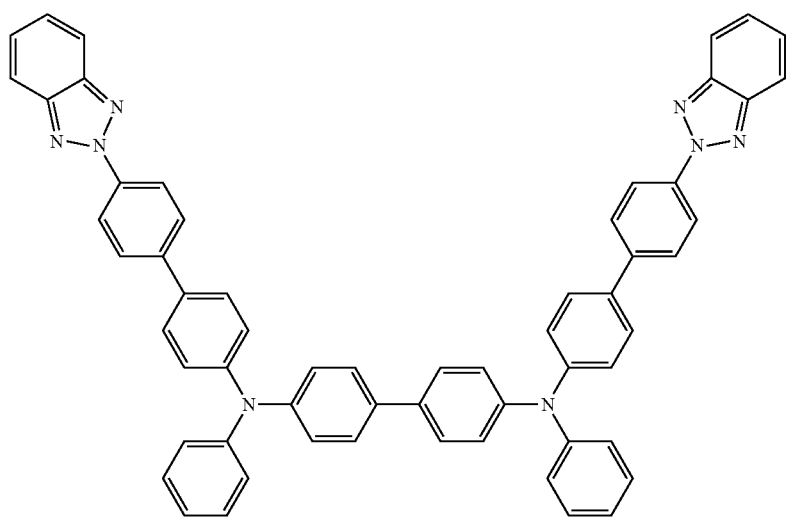
(1-9)
[Chem. 17]
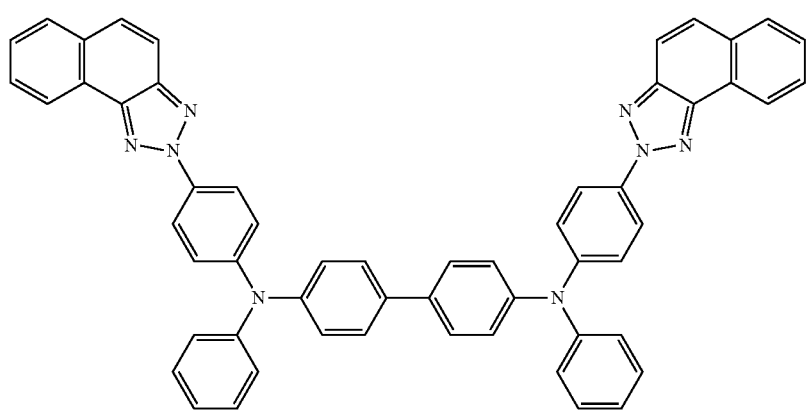
(1-10)

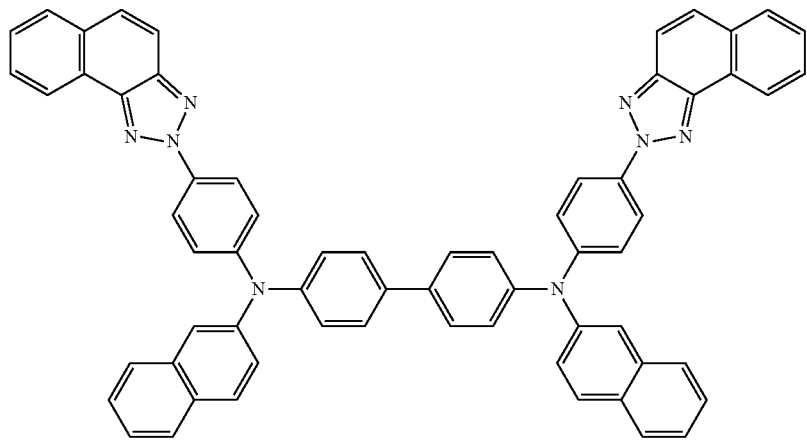
(1-11)
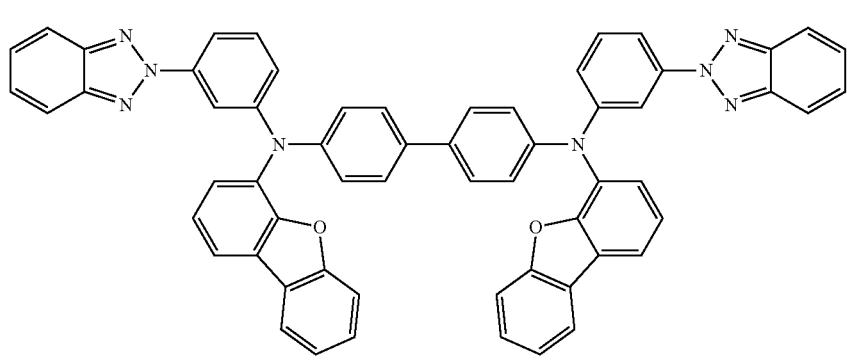
(1-12)
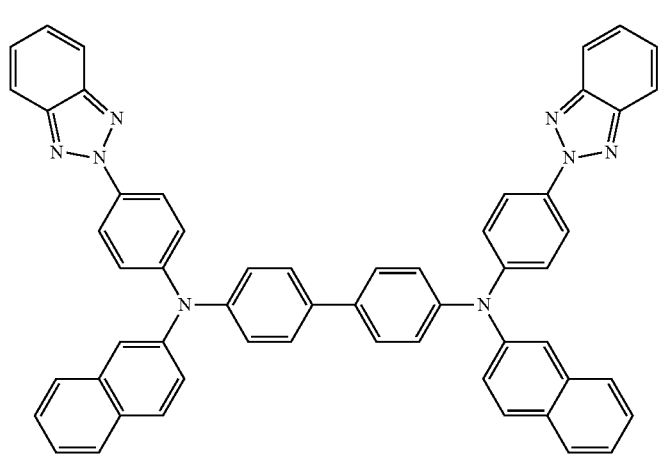
(1-13)

-continued
(1-14)
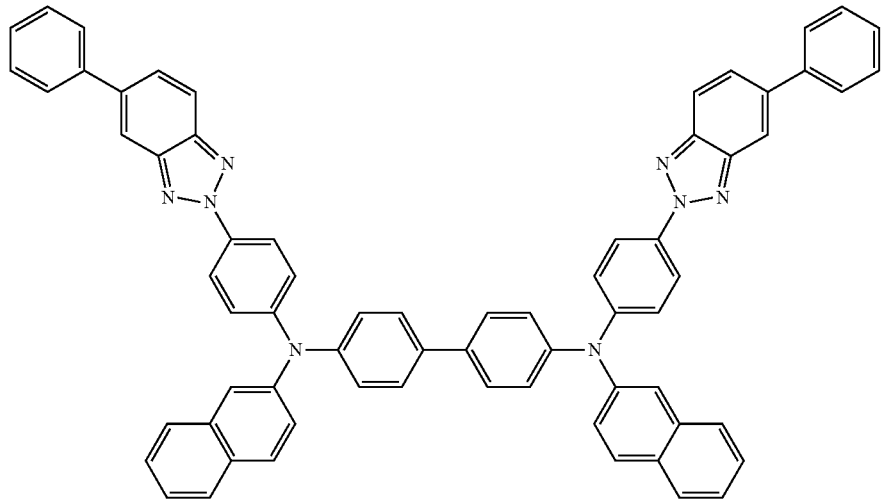
(1-15)
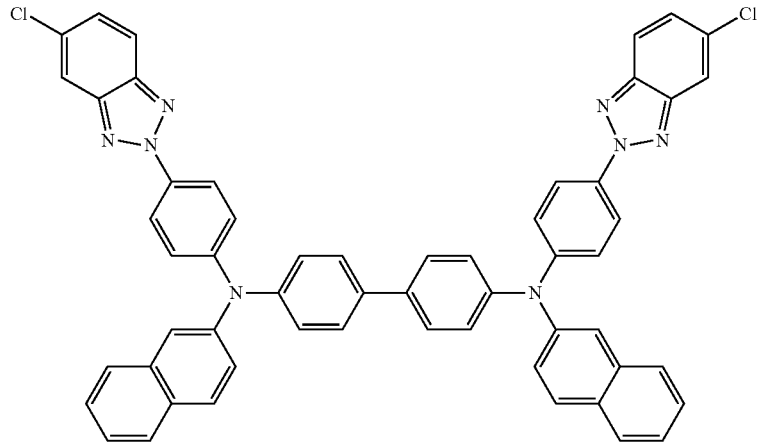
(1-16)
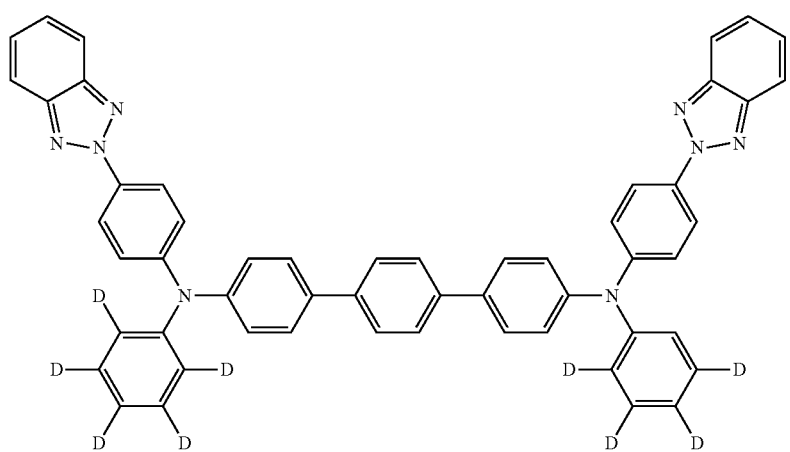

-continued
(1-17)
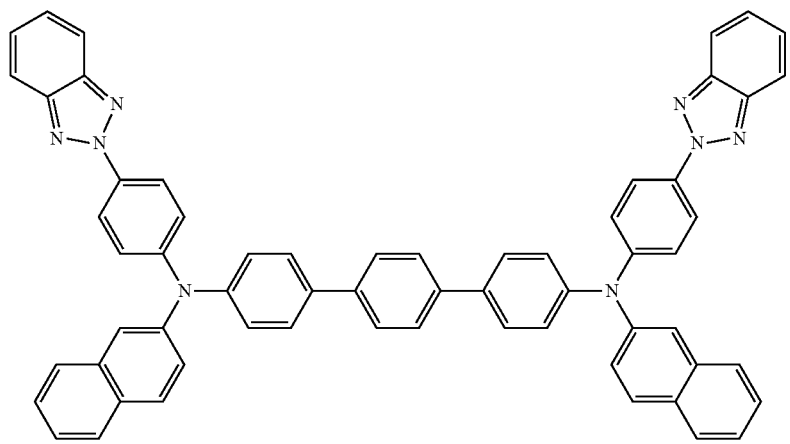
(1-18)
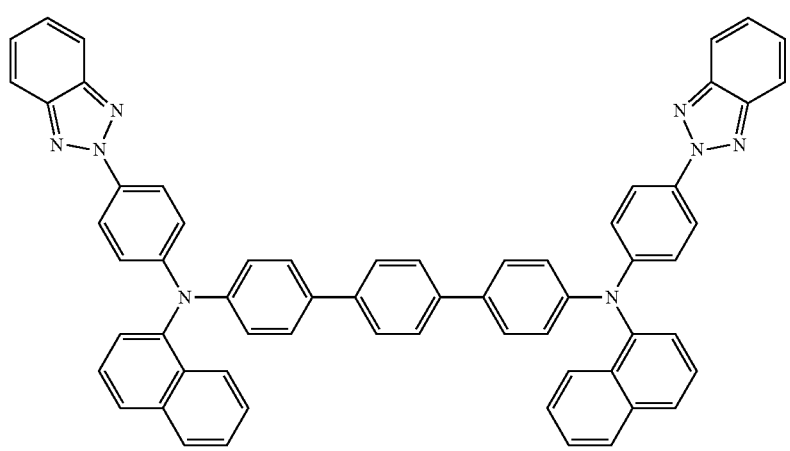
(1-19)
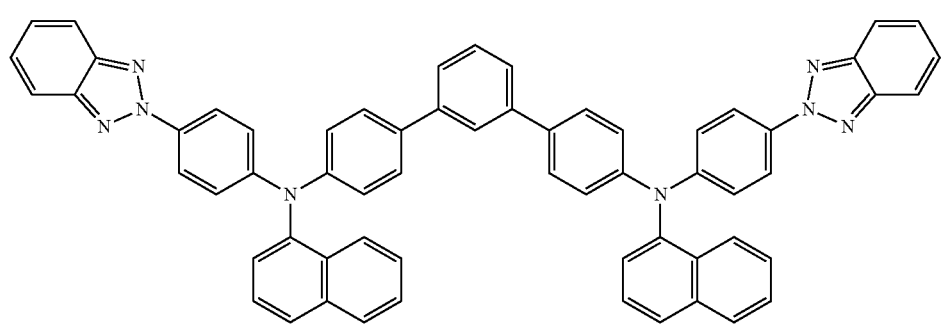

-continued
[Chem. 27]
(1-20)
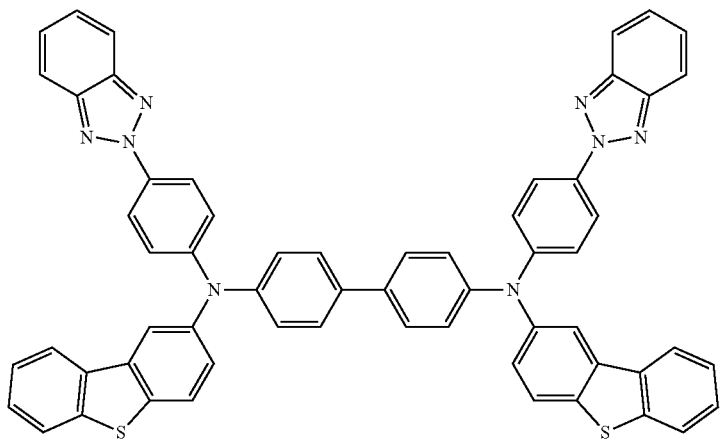
[Chem. 28]
(1-21)
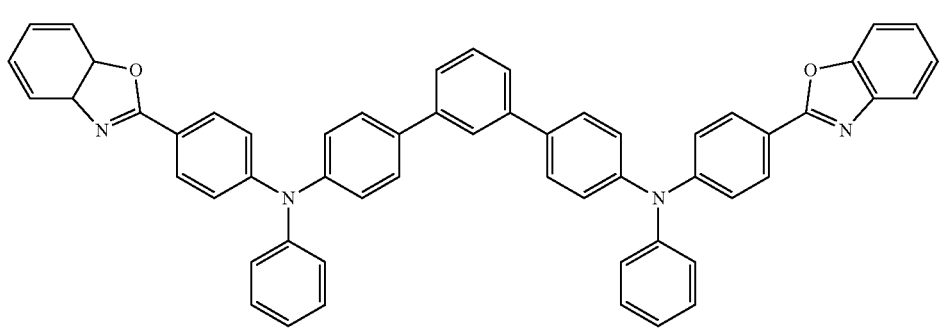
[Chem. 29]
(1-22)
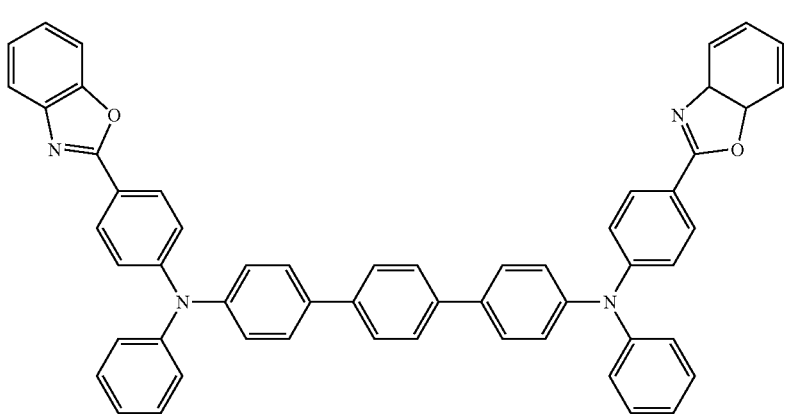

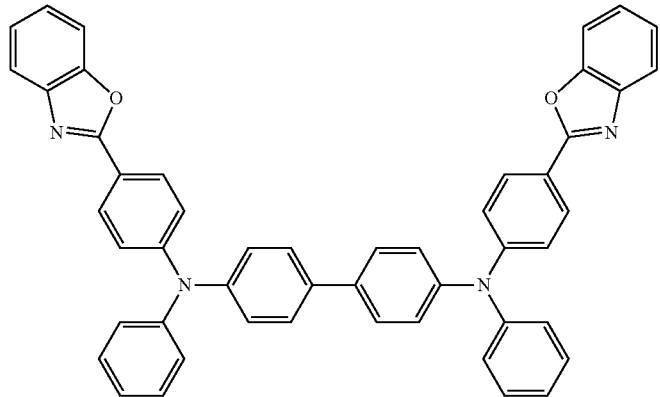
(1-23)
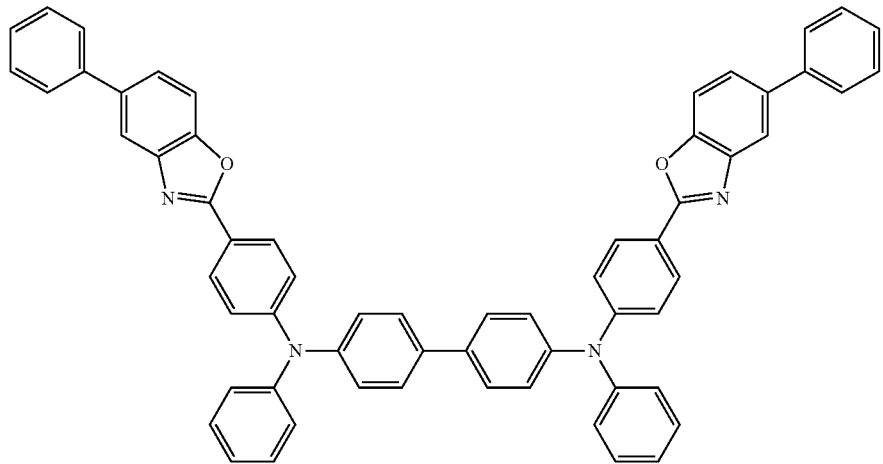
(1-24)
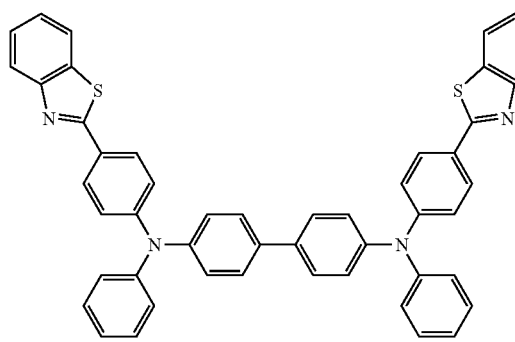
(1-25)
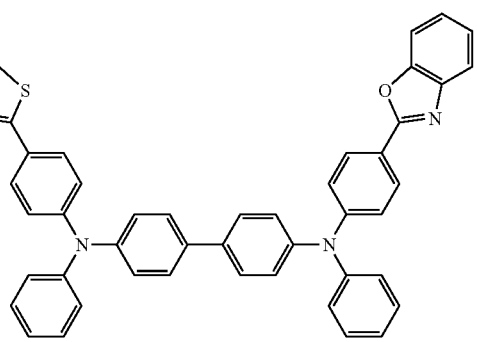
(1-26)

-continued
[Chem. 34]
(1-27)
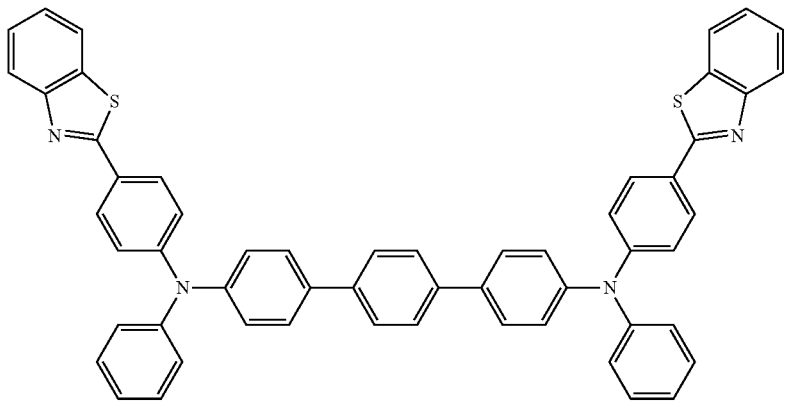
[Chem. 35]
(1-28)
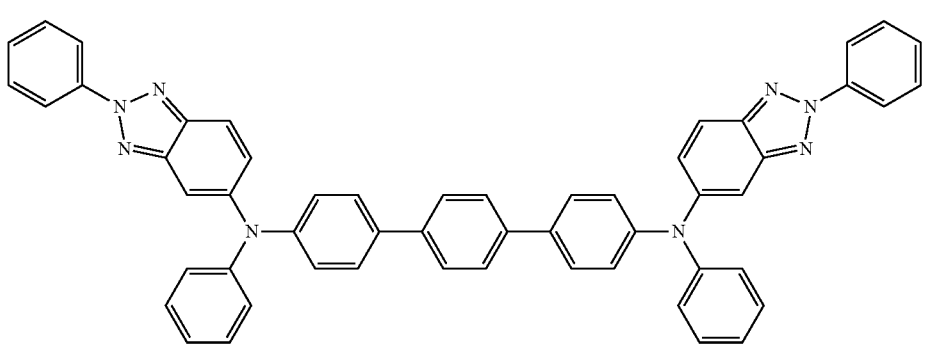
[Chem. 36]
(1-29)
[Chem. 37]
(1-30)
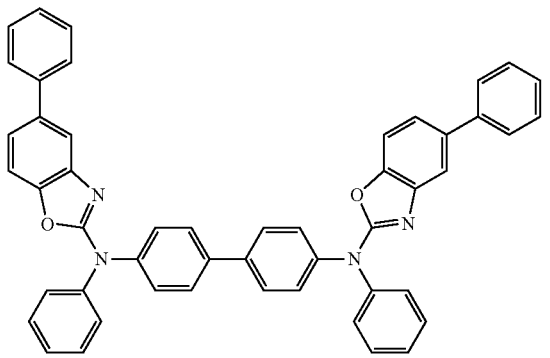
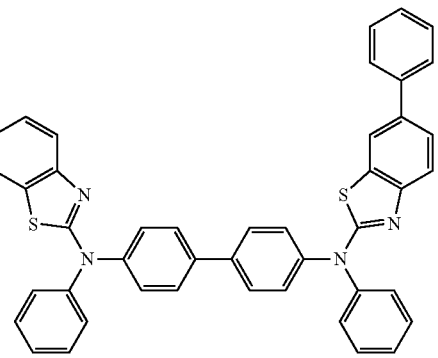

-continued
[Chem. 38]
(1-31)
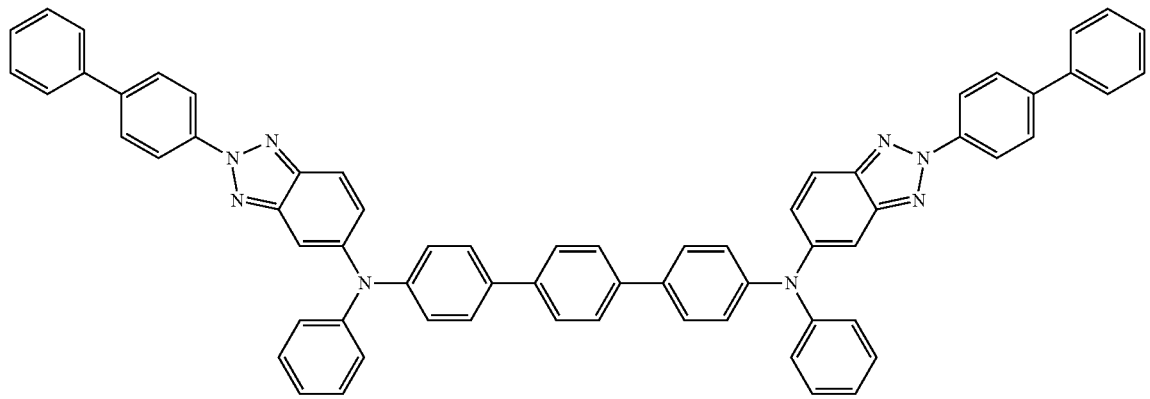
[Chem. 39]
(1-32)
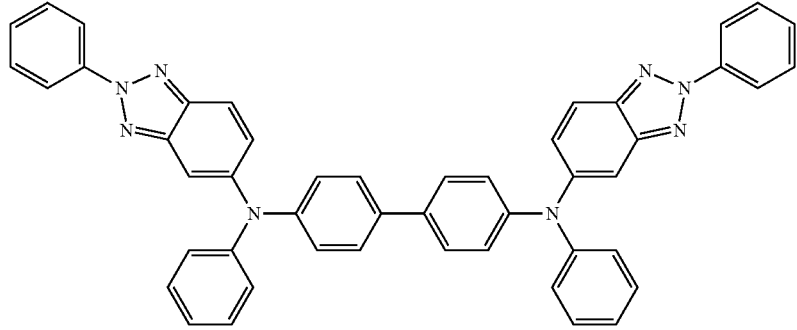
[Chem. 40]
(1-33)
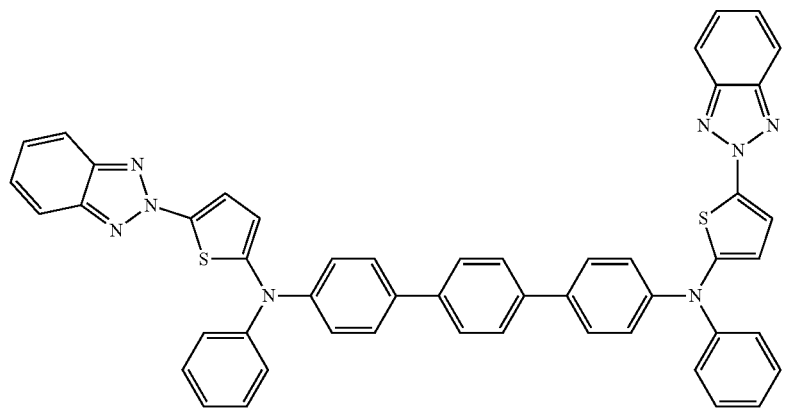
[Chem. 41]
(1-34)
[Chem. 42]
(1-35)
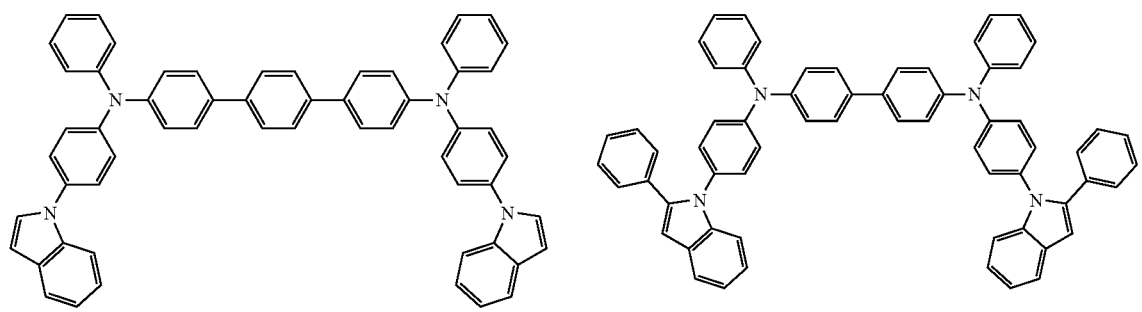

[Chem. 43]
(1-36)
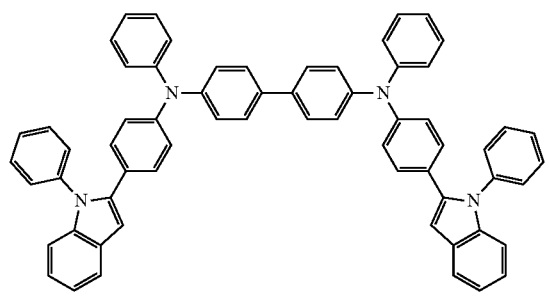
[Chem. 44]
(1-37)
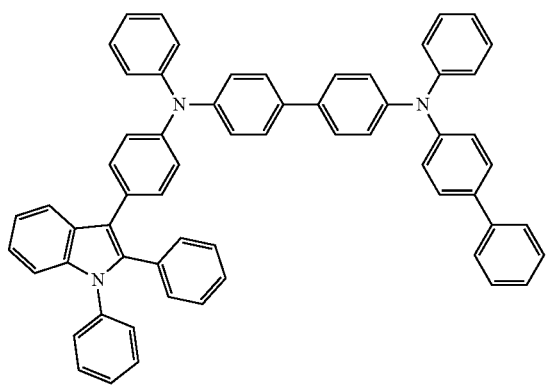
[Chem. 45]
(1-38)
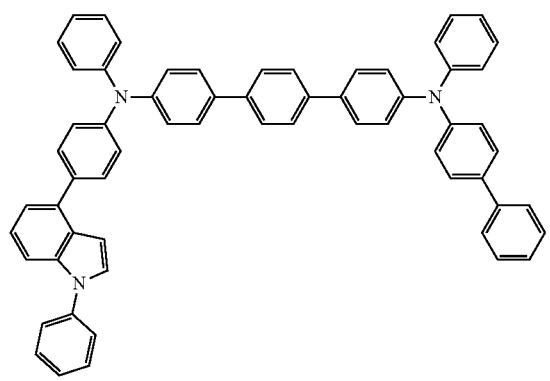
[Chem. 46]
(1-39)
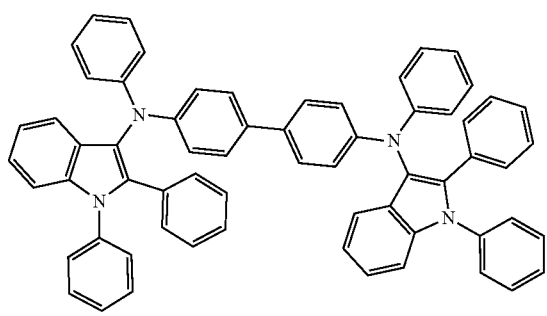
[Chem. 47]
(1-40)
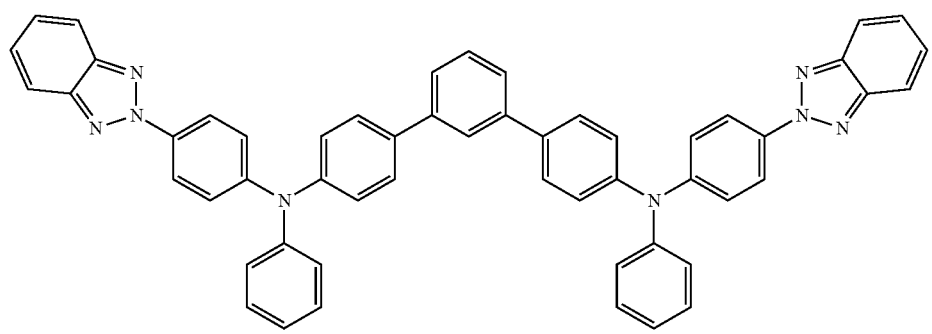

(1-41)
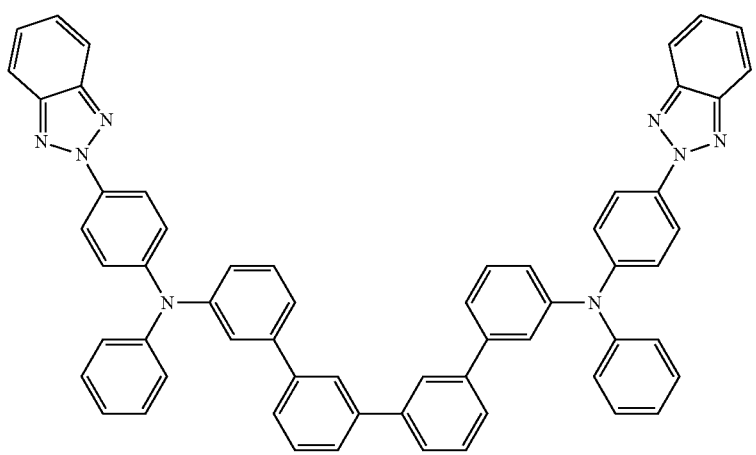
(1-42)
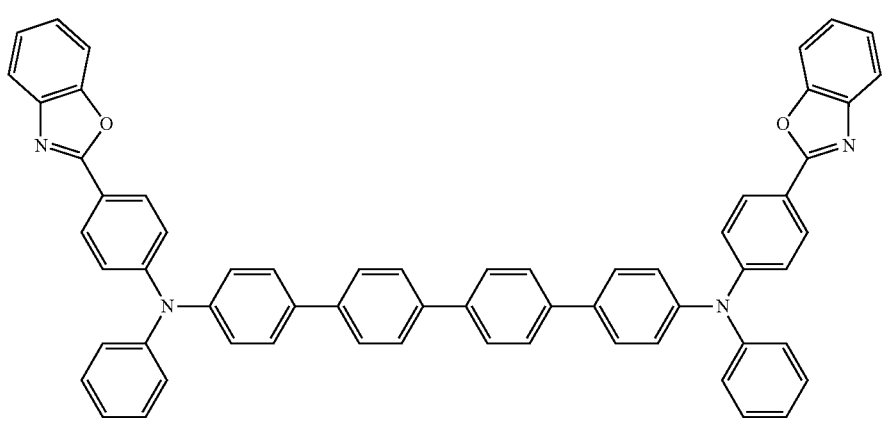
(1-43)
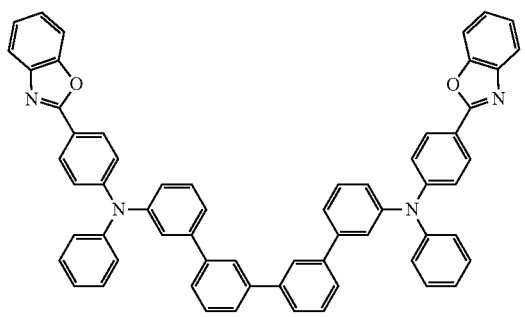
(1-44)
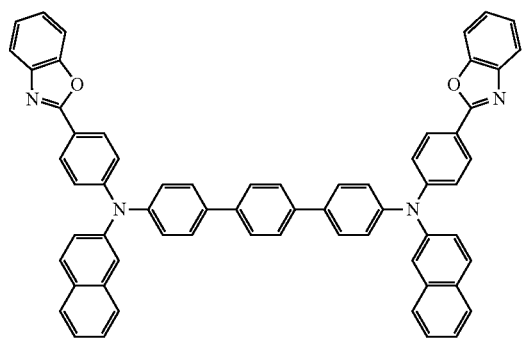

[Chem. 52]
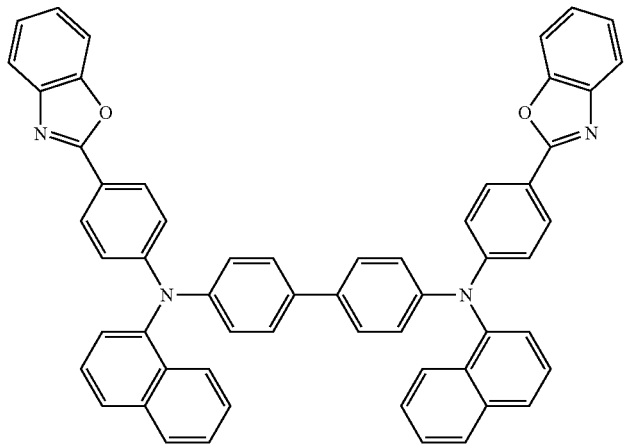
(1-45)
[Chem. 53]
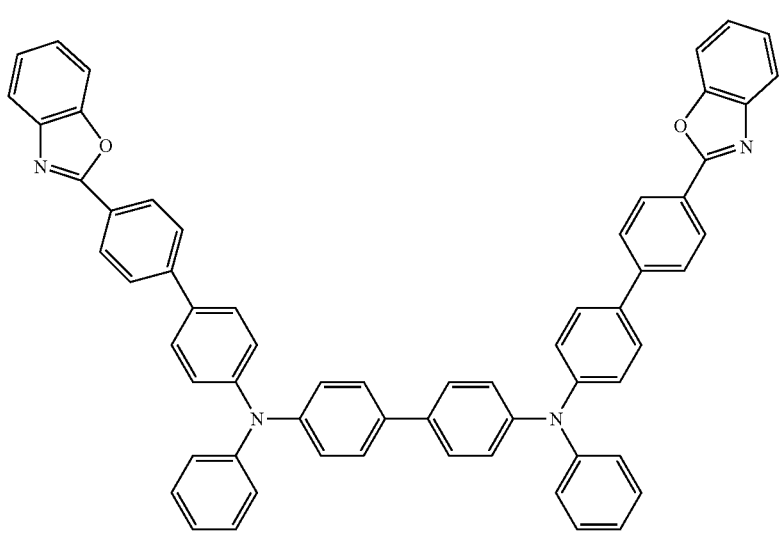
(1-46)
[Chem. 54]
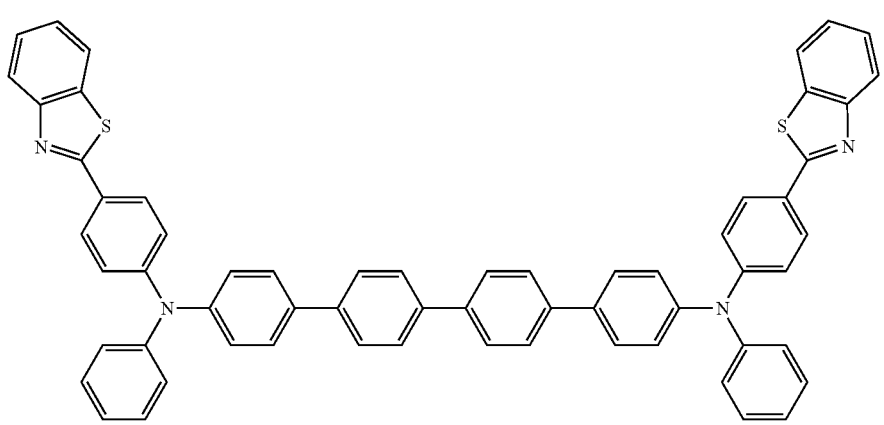
(1-47)

-continued
[Chem. 55]
(1-48)
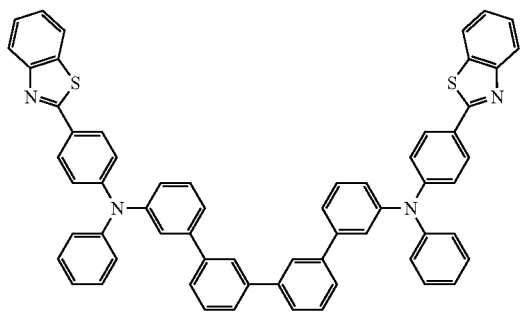
[Chem. 56]
(1-49)
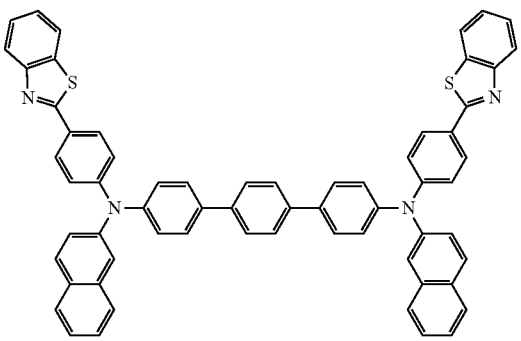
[Chem. 57]
(1-50)
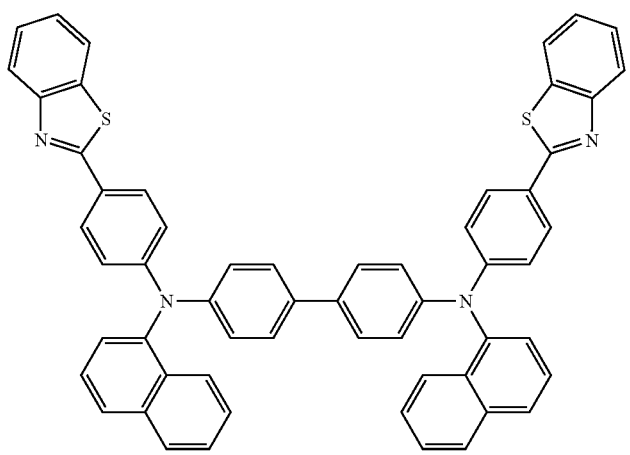
[Chem. 58]
(1-51)
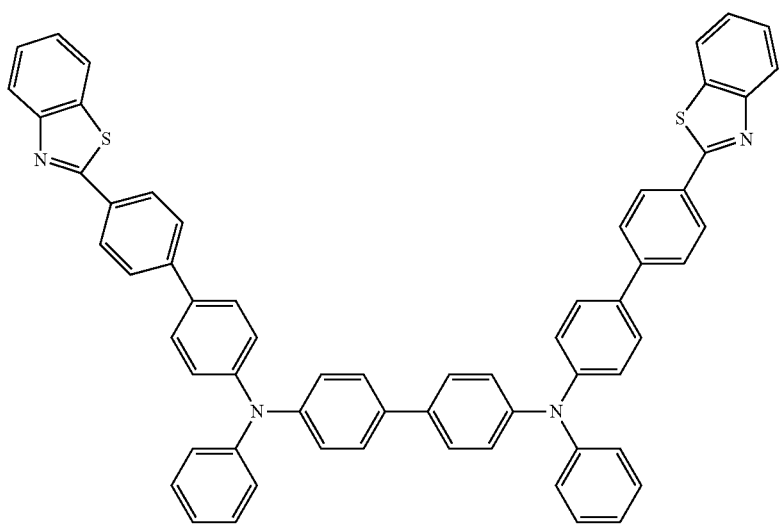

-continued
[Chem. 59]
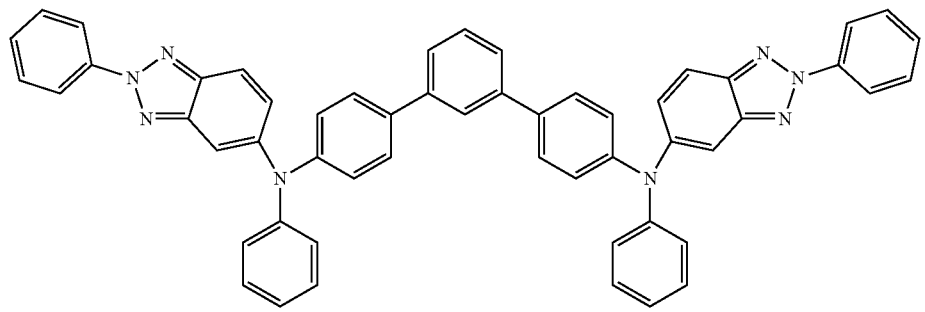
(1-52)
[Chem. 60]
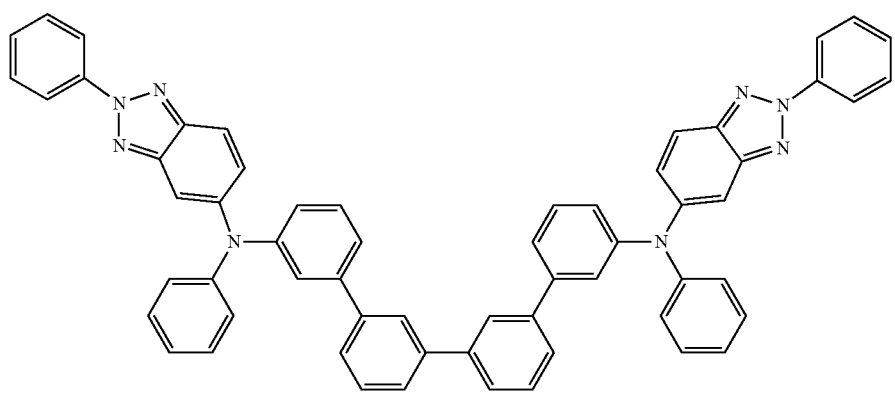
(1-53)
[Chem. 61]
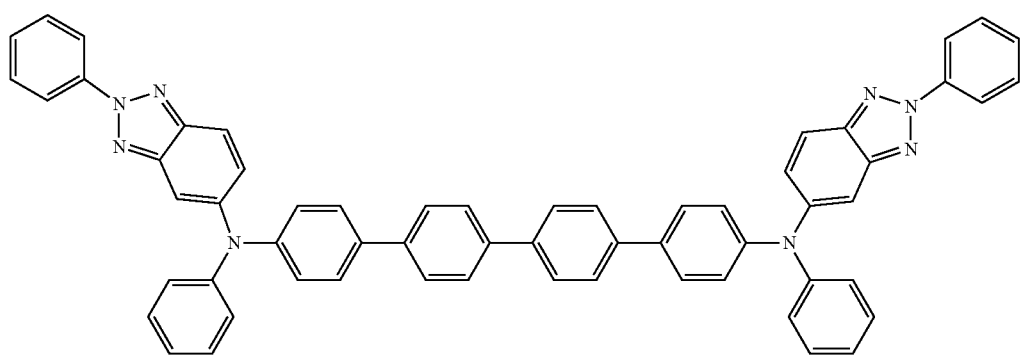
(1-54)
[Chem. 62]
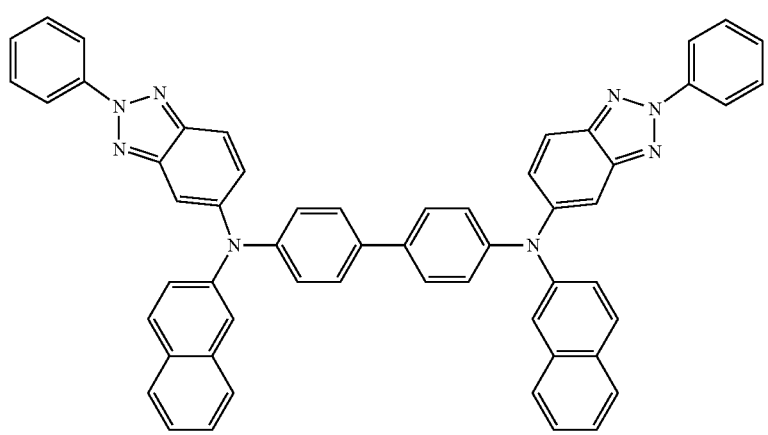
(1-55)

[Chem. 63]

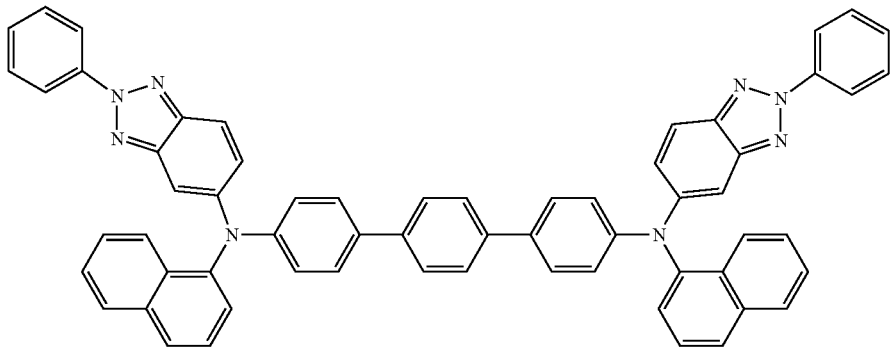

(1-56)

Purification of these compounds was performed by purification by column chromatography, adsorption purification by silica gel, activated carbon, activated clay, or the like, recrystallization with a solvent, a crystallization method, or the like, and finally, purification by sublimation purification or the like was performed. As the physical property values, the glass transition point (Tg) and the refractive index were measured. The glass transition point (Tg) is an index of stability of the thin film state, and the refractive index is an index regarding improvement in the light extraction efficiency.

The glass transition point (Tg) was measured by a high sensitivity differential scanning calorimeter (manufactured by Bruker AXS K.K., DSC3100S) using powder.

The refractive index and the extinction coefficient were measured by preparing a thin film of 80 nm on a silicon substrate and using a spectroscopic measurement apparatus (manufactured by Filmetrics, Inc., F10-RT-UV).

The absorbance was measured after adjusting the concentration to $10^{-5}$ mol/l with a toluene solution, and the absorption coefficient was measured by using an ultraviolet-visible-near infrared spectrophotometer (manufactured by JASCO, V-650) after adjusting the concentration to $5 \times 10^{-6}$ mol/l, $1 \times 10^{-5}$ mol/l, $1.5 \times 10^{-5}$ mol/l, and $2.0 \times 10^{-5}$ mol/l with a toluene solution.

Examples of the structure of the organic EL device of the present invention include light emitting devices having a top-emission structure in which: an anode formed of a metal, a hole transport layer, a light emitting layer, an electron transport layer, a semi-transparent cathode, and a capping layer are provided on a glass substrate in the stated order; a hole injection layer is provided between the anode and the hole transport layer; an electron blocking layer is provided between the hole transport layer and the light emitting layer; a hole blocking layer is provided between the light emitting layer and the electron transport layer; and an electron injection layer is provided between the electron transport layer and the cathode. In these multilayer structures, several layers of organic layers may be omitted or combined. For example, a configuration in which the hole transport layer and the electron blocking layer are combined, or a configuration in which the electron transport layer and the hole blocking layer are combined may be provided. The total film thickness of the layers of the organic EL device is favorably approximately 200 nm to 750 nm, and more favorably approximately 350 nm to 600 nm. Further, the film thickness of the capping layer is favorably, for example, 30 nm to 120 nm, and more favorably 40 nm to 80 nm. In this case, it is possible to achieve excellent light extraction efficiency. Note that the film thickness of the capping layer may be appropriately changed depending on the type of the light emitting material used for the light emitting device, the thickness of the organic EL device other than the capping layer, and the like.

As the anode of the organic EL device of the present invention, an electrode material having a large work function such as ITO and gold is used.

As the hole injection layer of the organic EL device of the present invention, an arylamine compound having a structure in which three or more triphenylamine structures are coupled by a single bond or a divalent group containing no hetero atom in the molecule, e.g., materials such as star-burst type triphenylamine derivatives and various triphenylamine tetramers, porphyrin compounds typified by copper phthalocyanine, acceptor heterocyclic compounds such as hexacyanoazatriphenylene, coating type polymer materials, and the like can be used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

As the hole transport layer of the organic EL device of the present invention, for example, N,N'-diphenyl-N,N'-di(m-tolyl) benzidine (hereinafter, abbreviated as TPD), N,N'-diphenyl-N,N'-di(α-naphthyl) benzidine (NPD), 1,1-bis[4-(di-4-tolylamino) phenyl] cyclohexane (TAPC), particularly, an arylamine compound having a structure in which two triphenylamine structures are coupled by a single bond or a divalent group containing no hetero atom in the molecule, e.g., N,N,N',N'-tetrabiphenylyl benzidine, is favorably used. Further, an arylamine compound having a structure in which three or more triphenylamine structures are coupled by a single bond or a divalent group containing no hetero atom in the molecule, e.g., various triphenylamine trimers or tetramers, is favorably used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

Further, in the hole injection layer or the hole transport layer, one obtained by P-doping a material typically used for the layer with trisbromophenylaminehexachloroantimony or the like, a polymer compound having a structure of a benzidine derivative as a partial structure, such as TPD, and the like can be used.

As the electron blocking layer of the organic EL device of the present invention, a compound having an electron blocking action, e.g., carbazol derivatives such as 4,4',4''-tri(N-carbazolyl)triphenylamine (hereinafter, abbreviated as TCTA), 9,9-bis[4-(carbazol-9-yl) phenyl] fluorene, 1,3-bis(carbazol-9-yl) benzene (hereinafter, abbreviated as mCP), 2,2-bis(4-carbazol-9-yl-phenyl) adamantine (Ad-Cz), and a compound having a triphenylsilyl group and a triarylamine structure typified by 9-[4-(carbazol-9-yl) phenyl]-9-[4-(triphenylsilyl) phenyl]-9H-fluorene, can be used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

As the light emitting layer of the organic EL device of the present invention, metal complexes of a quinolinol derivative including $Alq_3$, various metal complexes, anthracene derivatives, bisstyrylbenzene derivatives, pyrene derivatives, oxazole derivatives, polyparaphenylene vinylene derivatives, and the like can be used. Further, the light emitting layer may be formed of a host material and a dopant material. As the host material, in addition to the above-mentioned light-emitting material, a thiazole derivative, a benzimidazole derivative, a polydialkylfluorene derivative, and the like can be used. Further, as the dopant material, quinacridone, coumarin, rubrene, perylene, and derivatives thereof, benzopyran derivatives, rhodamine derivatives, aminostyryl derivatives, and the like can be used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided.

Further, as the light emitting material, also a phosphorescent material can be used. As the phosphorescent emitter, phosphorescent emitters of metal complexes such as iridium and platinum can be used. A green phosphorescent emitter such as $Ir(ppy)_3$, a blue phosphorescent emitter such as FIrpic and FIr6, a red phosphorescent emitter such as $Btp_2Ir(acac)$, and the like are used. At this time, as the hole injection/transport host material, 4,4'-di(N-carbazolyl)biphenyl (CBP), carbazol derivatives such as TCTA and mCP, and the like can be used. As the electron transport host material, p-bis(triphenylsilyl) benzene(UGH2), 2,2',2''-(1,3,5-phenylene)-tris(1-phenyl-1H-benzimidazole) (TPBI), and the like can be used, and it is possible to prepare a high performance organic EL device.

In order to avoid concentration quenching, it is favorable to dope the host material with the phosphorescent material by co-deposition in the range of 1 to 30 percent by weight with respect to the entire light emitting layer.

Further, as the light emitting material, a material that emits delayed fluorescence, e.g., CDCB derivatives such as PIC-TRZ, CC2TA, PXZ-TRZ, and 4CzIPN, can be used (see, for example, Non-Patent Literature 7).

These materials can be formed into thin films by a well-known method such as a spin coating method and an inkjet method in addition to a deposition method.

As the hole blocking layer of the organic EL device of the present invention, a compound having a hole blocking action, e.g., phenanthroline derivatives such as bathocuproine (BCP), metal complexes of quinolinol derivatives such as aluminum (III) bis(2-methyl-8-quinolinato)-4-phenylphenolate (hereinafter, abbreviated as BAlq), various rare earth complexes, triazole derivatives, triazine derivatives, oxadiazole derivatives, and the like can be used. These materials may also serve as the material of the electron transport layer. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

As the electron transport layer of the organic EL device of the present invention, metal complexes of quinolinol derivatives including $Alq_3$ and BAlq, various metal complexes, triazole derivatives, triazine derivatives, oxadiazole derivatives, thiadiazole derivatives, pyridoindole derivatives, carbodiimide derivatives, quinoxaline derivatives, phenanthroline derivatives, silole derivatives, and the like can be used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

As the electron injection layer of the organic EL device of the present invention, alkali metal salts such as lithium fluoride and cesium fluoride, alkaline earth metal salts such as magnesium fluoride, metal oxides such as aluminum oxide, and the like can be used. However, in favorable selection of the electron transport layer and the cathode, this can be omitted.

Further, in the electron injection layer or the electron transport layer, one obtained by N-doping a material typically used for the layer with metal such as cesium can be used.

As the electrode material of the semi-transparent cathode of the organic EL device of the present invention, electrode materials having a low work function such as aluminum, alloys having a further lower work function such as a magnesium silver alloy, a magnesium calcium alloy, a magnesium indium alloy, and an aluminum magnesium alloy, ITO, IZO, and the like are used.

As the capping layer of the organic EL device of the present invention, the arylamine compound represented by the above-mentioned general formula (1), and the like are preferably used. They may be deposited alone, but may be used as a single layer obtained by being mixed with other materials and deposited. Alternatively, a stacked structure including layers obtained by being deposited alone, layers obtained by being mixed with each other and deposited, or layers obtained by being mixed with a layer deposited alone and deposited may be provided. These materials can be formed into thin films by a well-known method such as a spin coating method and an inkjet method in addition to a deposition method.

Note that although the organic EL device having a top-emission structure has been described above, the present invention is not limited thereto, and can be similarly applied to the organic EL device having a bottom emission structure and the organic EL device having a dual emission structure in which light is emitted from both the top and the bottom. In these cases, the electrode in the direction in which light is extracted from the light emitting device to the outside needs to be transparent or semi-transparent.

The refractive index of the material forming the capping layer is favorably larger than the refractive index of an adjacent electrode. That is, the light extraction efficiency in the organic EL device is improved by the capping layer, and the effect is effective because the effect of light interference is larger as the reflectance at the interface between the capping layer and the material in contact with the capping layer is larger. Therefore, the refractive index of the material forming the capping layer is preferably larger than the refractive index of the adjacent electrode, only needs to be not less than 1.70, and is favorably not less than 1.80 and particularly favorably not less than 1.85.

Hereinafter, embodiments of the present invention will be specifically described with reference to examples. However, the present invention is not limited the following examples.

Example 1

Synthesis of N,N'-bis{4-(2H-benzo[1,2,3]triazole-2-yl)phenyl}-N,N'-diphenyl-4,4'-diamino-1,1'-biphenyl (Compound (1-1))

To a reaction vessel purged with nitrogen, 4.2 g of 2-(4-bromophenyl)-2H-benzo[1,2,3]triazole, 2.3 g of N,N'-diphenylbenzidine, 2.0 g of sodium tert-butoxide, and 50 ml of toluene were added, and nitrogen gas was caused to pass through the reaction vessel while applying ultrasonic waves for 30 minutes. Sixty two point zero mg of palladium acetate and 0.2 ml of tri-tert-butylphosphine were added thereto and heated, followed by stirring at 91° C. for 5 hours. After cooling to room temperature, 50 ml of toluene was added, and an extraction operation was performed, thereby collecting an organic layer. The organic layer was concentrated, and then purified by column chromatography (carrier: NH silica gel, eluent: toluene n-hexane). Further, by performing dispersion washing using 100 ml of n-hexane, 3.3 g (yield of 66%) of yellow powder of N,N'-bis{4-(2H-benzo[1,2,3] triazole-2-yl)phenyl}-N,N'-diphenyl-4,4'-diamino-1,1'-biphenyl (compound (1-1)) was obtained.

The structure of the obtained yellow powder was identified using NMR.

The following 34 hydrogen signals ware detected by $^1$H-NMR (THF-$d_8$).

δ(ppm)=8.26 (4H), 7.89 (4H), 7.60 (4H), 7.39 (4H), 7.33 (4H), 7.24 (4H), 7.21 (8H), 7.10 (2H).

Example 2

Synthesis of N,N'-bis {4-(2H-benzo[1,2,3]triazole-2-yl)phenyl}-N,N'-diphenyl-4,4''-diamino-1,1':4',1''-terphenyl (Compound (1-2))

To a reaction vessel purged with nitrogen, 14.0 g of 4,4''-diiodo-1,1':4',1''-terphenyl, 18.3 g of {4-(2H-benzo[1, 2,3]triazole-2-yl)phenyl}phenylamine, 13.2 g of potassium carbonate, 0.3 g of copper powder, 0.9 g of sodium bisulfite, 0.7 g of 3,5-di-tert-butylsalicylic acid, and 30 ml of dodecylbenzene were added, heated, and stirred at 210° C. for 44 hours. After cooling to room temperature, 50 ml of toluene was added, and the precipitate was collected by filtration. Two hundred thirty ml of 1,2-dichlorobenzene was added to the precipitate and dissolved by heating, and the insoluble matter was removed by hot filtration. The filtrate was concentrated, and crystallization purification using 1,2-dichlorobenzene was performed. After that, by performing dispersion washing using methanol, 22.2 g (yield of 96%) of yellow powder of N,N'-bis{4-(2H-benzo[1,2,3]triazole-2-yl)phenyl}-N,N'-diphenyl-4,4''-diamino-1,1':4',1''-terphenyl (compound (1-2)) was obtained.

The structure of the obtained yellow powder was identified using NMR.

The following 38 hydrogen signals ware detected by $^1$H-NMR (CDCl$_3$).

δ (ppm)=8.24 (4H), 7.99-7.92 (4H), 7.72-7.58 (7H), 7.50-7.12 (23H).

Example 3

Synthesis of N,N'-bis {4-(benzoxazole-2-yl)phenyl}-N,N'-diphenyl-4,4''-diamino-1,1': 4',1''-terphenyl (Compound (1-22))

In Example 1, instead of {4-(2H-benzo[1,2,3]triazole-2-yl)phenyl}phenylamine, {4-(benzoxazole-2-yl) phenyl}phenylamine was used, and reaction was caused to occur under similar conditions, thereby obtaining 12.4 g (yield of 47%) of yellow powder of N,N'-bis{4-(benzoxazole-2-yl)phenyl}-N,N'-diphenyl-4,4''-diamino-1,1':4',1''-terphenyl (compound (1-22)).

The structure of the obtained yellow powder was identified using NMR.

The following 38 hydrogen signals ware detected by $^1$H-NMR (CDCl$_3$).

δ (ppm)=8.13 (4H), 7.80-7.55 (11H), 7.50-7.16 (23H).

Example 4

Synthesis of N,N'-bis{4-(benzoxazole-2-yl)phenyl}-N,N'-diphenyl-4,4'-diamino-1,1'-biphenyl (Compound (1-23))

In Example 1, instead of 2-(4-bromophenyl)-2H-benzo[1, 2,3]triazole, 2-(4-bromophenyl)-benzoxazole was used, and reaction was caused to occur under similar conditions, thereby obtaining 8.8 g (yield of 54%) of light yellow powder of N,N'-bis{4-(benzoxazole-2-yl)phenyl}-N,N'-diphenyl-4,4'-diamino-1,1'-biphenyl (compound (1-23)).

The structure of the obtained light yellow powder was identified using NMR.

The following 34 hydrogen signals ware detected by $^1$H-NMR (CDCl$_3$).

δ (ppm)=8.12 (4H), 7.80-7.72 (2H), 7.60-7.53 (5H), 7.41-7.14 (23H).

Example 5

Synthesis of N,N'-bis {4-(benzothiazole-2-yl)phenyl}-N,N'-diphenyl-4,4'-diamino-1,1'-biphenyl (Compound (1-25))

In Example 1, instead of 2-(4-bromophenyl)-2H-benzo[1, 2,3]triazole, 2-(4-bromophenyl)-benzothiazole was used, and reaction was performed under similar conditions, thereby obtaining 9.3 g (yield of 62%) of light yellow powder of N,N'-bis{4-(benzothiazole-2-yl)phenyl}-N,N'-diphenyl-4,4'-diamino-1,1'-biphenyl (compound (1-25)).

The structure of the obtained light yellow powder was identified using NMR.

The following 34 hydrogen signals ware detected by $^1$H-NMR (CDCl$_3$).

δ (ppm)=8.10-7.88 (8H), 7.60-7.13 (26H).

Example 6

Synthesis of N,N'-bis{4-(benzothiazole-2-yl)phenyl}-N,N'-diphenyl-4,4"-diamino-1,1':4',1"-terphenyl (Compound (1-27))

To a reaction vessel purged with nitrogen, 9.3 g of N-{4-(benzothiazole-2-yl)phenyl}phenylamine, 7.1 g of 4,4"-diiodo-1,1': 4',1"-terphenyl, 4.6 g of sodium tert-butoxide, and 140 ml of toluene were added, and nitrogen gas was caused to pass through the reaction vessel while applying ultrasonic waves for 30 minutes. Zero point two zero g of palladium acetate and 0.5 g of 50% (v/v) toluene solution of tert-butylphosphine were added thereto and heated, followed by heated under reflux for 3 hours while stirring. After cooling to room temperature, the precipitate was collected by filtration. After that, by repeating crystallization purification using a mixed solvent of 1,2-dichlorobenzene/methanol, 7.0 g (yield of 58%) of yellower powder of N,N'-bis{4-(benzothiazole-2-yl)phenyl}-N,N'-diphenyl-4,4"-diamino-1,1': 4',1"-terphenyl (compound (1-27)) was obtained.

The structure of the obtained yellow powder was identified using NMR.

The following 38 hydrogen signals ware detected by $^1$H-NMR (THF-d$_8$).

δ (ppm)=8.07-7.88 (8H), 7.70-7.60 (8H), 7.54-7.46 (2H), 7.40-7.15 (20H).

Example 7

The glass transition point of the compound of the present invention was obtained by using a high sensitivity differential scanning calorimeter (manufactured by Bruker AXS K.K., DSC3100S).

Glass Transition Point

Example compound (1-1) 125° C.
Example compound (1-2) 135° C.
Example compound (1-22) 137° C.
Example compound (1-23) 128° C.
Example compound (1-25) 127° C.
Example compound (1-27) 137° C.

The compound of the present invention has a glass transition point of not less than 100° C. This indicated that the thin film state is stable in the compound of the present invention.

Example 8

A deposited film having a film thickness of 80 nm was prepared on a silicon substrate by using the compound of the present invention, and a refractive index n and an extinction coefficient k at the wavelengths of from 400 nm and 410 nm were measured by using a spectroscopic measurement apparatus (manufactured by Filmetrics, Inc., F10-RT-UV). For comparison, measurement was performed also for comparative compounds (2-1) and (2-2) of the following structural formulae (see, for example, Patent Literature 3). The measurement results are summarized in Table 1 and shown.

[Chem. 64]

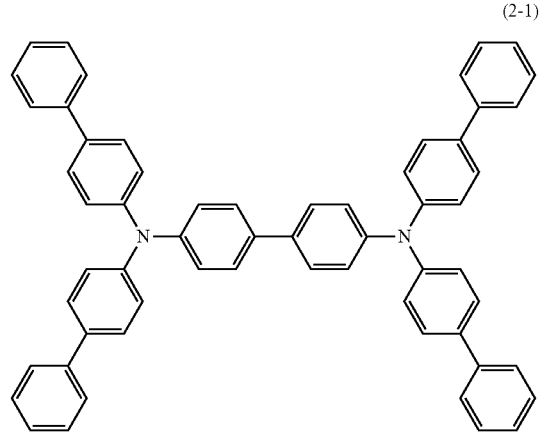

(2-1)

[Chem. 65]

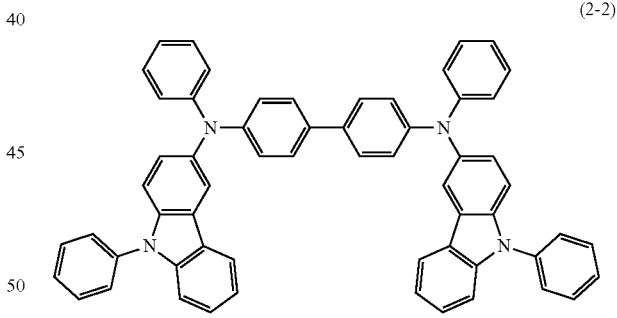

(2-2)

TABLE 1

|  | Refractive index n (λ: 400 nm) | Refractive index n (λ: 410 nm) | Refractive index n (λ: 430 nm) | Extinction coefficient k (λ: 400 nm) | Extinction coefficient k (λ: 410 nm) | Extinction coefficient k (λ: 430 nm) |
|---|---|---|---|---|---|---|
| Example compound (1-1) | 2.18 | 2.34 | 2.42 | 0.75 | 0.62 | 0.27 |
| Example compound (1-2) | 2.23 | 2.38 | 2.41 | 0.75 | 0.59 | 0.24 |
| Example compound (1-22) | 2.48 | 2.54 | 2.39 | 0.70 | 0.43 | 0.11 |
| Example compound (1-23) | 2.50 | 2.54 | 2.41 | 0.69 | 0.43 | 0.14 |

TABLE 1-continued

| | Refractive index n (λ: 400 nm) | Refractive index n (λ: 410 nm) | Refractive index n (λ: 430 nm) | Extinction coefficient k (λ: 400 nm) | Extinction coefficient k (λ: 410 nm) | Extinction coefficient k (λ: 430 nm) |
| --- | --- | --- | --- | --- | --- | --- |
| Example compound (1-25) | 2.23 | 2.43 | 2.47 | 0.84 | 0.67 | 0.26 |
| Example compound (1-27) | 2.26 | 2.45 | 2.45 | 0.83 | 0.63 | 0.23 |
| Comparative Example (2-1) | 2.26 | 2.20 | 2.10 | 0.21 | 0.13 | 0.05 |
| Comparative Example (2-2) | 2.13 | 2.10 | 1.99 | 0.15 | 0.06 | 0.00 |

As described above, the compound of the present invention has a value equal to or larger than the refractive indices of the comparative compounds (2-1) and (2-2). From this, it is expected that the light extraction efficiency in the organic EL device can be improved. Further, while the extinction coefficient at the wavelengths of from 400 nm to 410 nm is not more than 0.3 in the comparative compounds (2-1) and (2-2), the compound of the present invention has a larger value. This indicates that light having the wavelengths of from 400 nm to 410 nm from sunlight is absorbed well, which does not affect the material inside the device.

Example 9

Using the compound of the present invention, the absorbance at the wavelengths of from 400 nm and 410 nm was measured after adjusting the concentration to $10^{-5}$ mol/l with a toluene solution, and the absorption coefficient was measured from calibration curve by using an ultraviolet-visible-near infrared spectrophotometer (manufactured by JASCO, V-650) after adjusting the 4 kinds of concentration to $5 \times 10^{-6}$ mol/l, $1 \times 10^{-5}$ mol/l, $1.5 \times 10^{-5}$ mol/l, and $2.0 \times 10^{-5}$ mol/l with a toluene solution. For comparison, measurement was performed also for the comparative compound (2-2) of the above-mentioned structural formula. The measurement results are summarized in Table 2 and shown.

TABLE 2

| | Peak wavelength λ max | Absorbance (λ: 400 nm) | Absorbance (λ: 410 nm) | Absorption coefficient |
| --- | --- | --- | --- | --- |
| Example compound (1-1) | 390 nm | 0.617 | 0.480 | 64905 |
| Example compound (1-2) | 388 nm | 0.739 | 0.533 | 78155 |
| Example compound (1-22) | 380 nm | 0.548 | 0.201 | 89074 |
| Example compound (1-23) | 380 nm | 0 526 | 0.224 | 77112 |
| Example compound (1-25) | 390 nm | 0.724 | 0.515 | 76682 |
| Example compound (1-27) | 388 nm | 0.841 | 0.535 | 89422 |
| Comparative Example (2-2) | 358 nm | 0.074 | 0.018 | 48856 |

As described above, while the absorbance at the wavelengths of from 400 nm to 410 nm is not more than 0.1 in the comparative compound (2-2), the compound of the present invention has a larger value of not less than 0.2. This indicates that light having the wavelengths of from 400 nm to 410 nm from sunlight is absorbed better. Further, while the absorption coefficient of the comparative compound (2-2) is 48856, the compound of the present invention has a larger value. This indicates that light is absorbed well under the same concentration condition. Regarding also the thin film, it is shown that light is absorbed better as the film thickness is increased, and a material having excellent light resistance is provided.

Example 10

As shown in FIG. 1, the organic EL device was prepared by forming a reflective ITO electrode as a metal anode 2 on a glass substrate 1 in advance and depositing a hole injection layer 3, a hole transport layer 4, a light emitting layer 5, an electron transport layer 6, an electron injection layer 7, a cathode 8, and a capping layer 9 thereon in the stated order.

Specifically, the glass substrate 1 obtained by depositing ITO having the film thickness of 50 nm, a silver alloy reflective film having a film thickness of 100 nm, and ITO having a film thickness of 5 nm in the stated order was ultrasonically cleaned in isopropyl alcohol for 20 minutes, and then dried on a hot plate heated to 250° C. for 10 minutes. Then, after performing UV ozone treatment for 2 minutes, this glass substrate with ITO was mounted in a vacuum deposition apparatus, and depressurized to not more than 0.001 Pa. Subsequently, the hole injection layer 3 was formed so as to cover the transparent anode 2, by performing binary deposition of an electron acceptor (Acceptor-1) of the following structural formula and a compound (3-1) of the following structural formula at the deposition rate at which the deposition rate ratio was Acceptor-1:Compound (3-1)= 3:97. On this hole injection layer 3, the compound (3-1) of the following structural formula was formed as the hole transport layer 4 so that the film thickness was 140 nm. On this hole transport layer 4, the light emitting layer 5 was formed by performing binary deposition of a compound (3-2) of the following structural formula and a compound (3-3) of the following structural formula at the deposition rate at which the deposition rate ratio was (3-2):(3-3)=5:95 so that the film thickness was 20 nm. On this light emitting layer 5, the electron transport layer 6 was formed by performing binary deposition of a compound (3-4) of the following structural formula and a compound (3-5) of the following structural formula at the deposition rate at which the deposition rate ratio was (3-4):(3-5)=50:50 so that the film thickness was 30 nm. On this electron transport layer 6, lithium fluoride was formed as the electron injection layer 7 so that the film thickness was 1 nm.

On this electron injection layer 7, a magnesium silver alloy was formed as the cathode 8 so that the film thickness was 12 nm. Finally, the compound (1-22) of the Example 3 was formed as the capping layer 9 so that the film thickness was 60 nm. The characteristics of the prepared organic EL device were measured at ambient temperature in the atmosphere.

The measurement results of the light emission characteristics obtained by applying DC voltage to the prepared organic EL device are summarized in Table 3 and shown.

[Chem. 66]

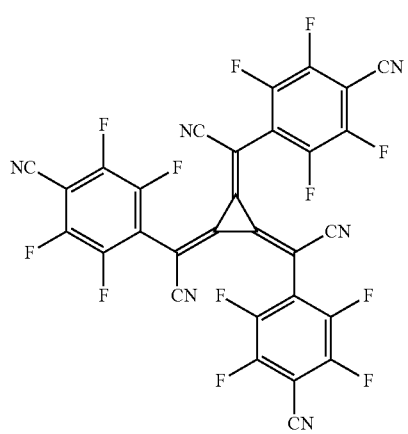

(Acceptor-1)

[Chem. 67]

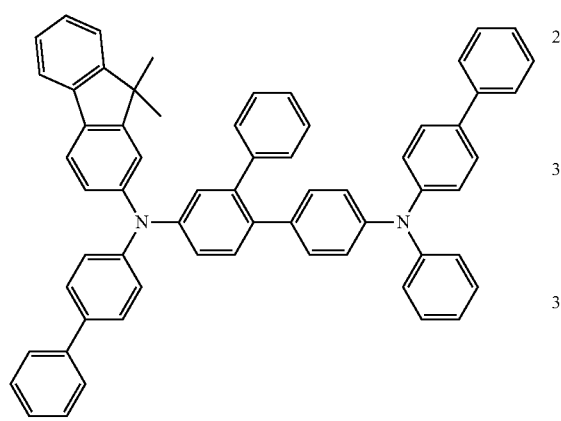

(3-1)

[Chem. 68]

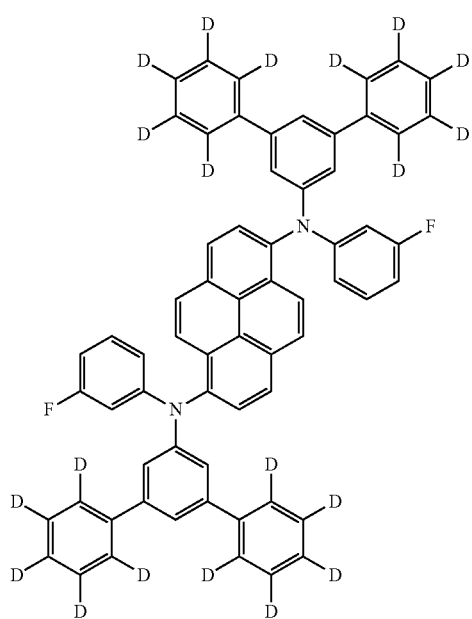

(3-2)

[Chem. 69]

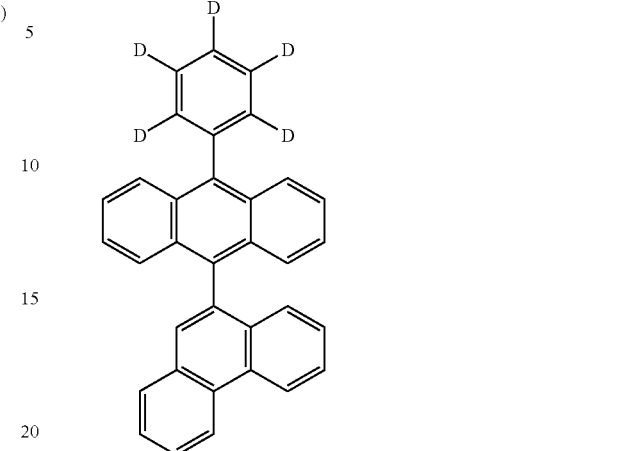

(3-3)

[Chem. 70]

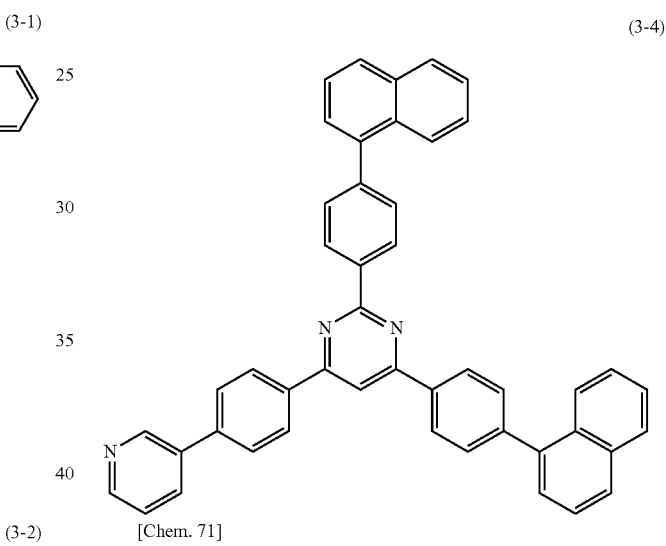

(3-4)

[Chem. 71]

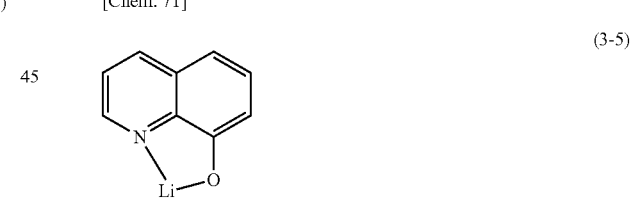

(3-5)

Example 11

An organic EL device was prepared under similar conditions to the Example 10 except that instead of the compound (1-22) of the Example 3, the compound (1-23) of the Example 4 was formed as the capping layer 9 so that the film thickness was 60 nm. The characteristics of the prepared organic EL device were measured at ambient temperature in the atmosphere. The measurement results of the light emission characteristics obtained by applying DC voltage to the prepared organic EL device are summarized in Table 3 and shown.

Comparative Example 1

For comparison, an organic EL device was prepared under similar conditions to the Example 10 except that instead of the compound (1-23) of the Example 4, the comparative compound (2-2) of the above-mentioned structural formula was formed as the capping layer 9 so that the film thickness was 60 nm. The characteristics of the prepared organic EL device were measured at ambient temperature in the atmosphere. The measurement results of the light emission characteristics obtained by applying DC voltage to the prepared organic EL device are summarized in Table 3 and shown.

The results of measuring the device lifetime of the prepared organic EL devices in the Example 10, Example 11, and Comparative Example 1 are summarized in Table 3 and shown. The device lifetime was measured as a period to the time when the luminance was attenuated from 100% (initial luminance) to 95% at the constant current driving of 10 mA/cm$^2$.

TABLE 3

| | Capping layer | Voltage[V] (10 mA/cm$^2$) | Luminance[cd/m$^2$] (10 mA/cm$^2$) | Light emission efficiency[cd/A] (10 mA/cm$^2$) | Power efficiency [1 m/W] (10 mA/cm$^2$) | Device lifetime 95% attenuation |
|---|---|---|---|---|---|---|
| Example 10 | Example compound (1-22) | 3.62 | 701 | 7.01 | 6.08 | 152 hours |
| Example 11 | Example compound (1-23) | 3.64 | 709 | 7.09 | 6.12 | 164 hours |
| Comparative Example 1 | Comparative compound (2-2) | 3.61 | 675 | 6.75 | 5.87 | 99 hours |

As shown in Table 3, while the driving voltages at the current density of 10 mA/cm$^2$ were substantially equal to each other in the device of the Comparative Example 1 using the comparative compound (2-2) and the devices of the Example 10 and Example 11, the luminance, light emission efficiency, power efficiency, and lifetime of the devices of the Example 10 and Example 11 were improved as compared with that of the device of the Comparative Example 1 using the comparative compound (2-2). This indicates that by the capping layer containing a material that has a high refractive index and is suitably used for the organic EL device of the present invention, it is possible to significantly improve the light extraction efficiency.

INDUSTRIAL APPLICABILITY

As described above, since the arylamine compound represented by the general formula (1), which is suitably used for the organic EL device of the present invention, has a high absorption coefficient and a high refractive index, and is capable of significantly improving the light extraction efficiency, and the thin film state thereof is stable, it is excellent as a compound for an organic EL device. By preparing an organic EL device using the compound, it is possible to achieve high efficiency and improve the durability and light resistance while absorbing light from sunlight so as not to affect the material inside the device. Further, by using the compound that does not absorb light in the blue, green, and red wavelength range, it is particularly suitable in the case that it is desired to display a clear and bright image with high color purity. For example, it becomes possible to develop it for home electric appliances and lighting applications.

REFERENCE SIGNS LIST

1 glass substrate
2 metal anode
3 hole injection layer
4 hole transport layer
5 light emitting layer
6 electron transport layer
7 electron injection layer
8 cathode
9 capping layer

The invention claimed is:
1. An organic electroluminescence device comprising: at least
an anode electrode;
a hole transport layer;
a light emitting layer;
an electron transport layer;
a cathode electrode; and
a capping layer in the stated order,
wherein the capping layer includes a material having an extinction coefficient of not less than 0.3 at wavelengths of from 400 nm to 410 nm and an absorbance of not less than 0.2 at wavelengths of from 400 nm to 410 nm in the absorption spectrum of a concentration of 10$^{-5}$ mol/l,
wherein the capping layer includes an arylamine compound represented by a following general formula (1):

[Chem. 1]

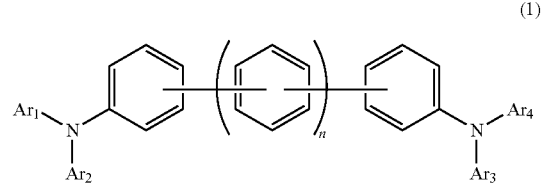

(1)

where, in the general formula (1), Ar$_1$, Ar$_2$, Ar$_3$, and Ar$_4$ may be the same or different from each other and each represents a substituted or unsubstituted aromatic hydrocarbon group, a substituted or unsubstituted aromatic heterocyclic group, or a substituted or unsubstituted condensed polycyclic aromatic group, n represents an integer of 0 to 4, wherein at least one of Ar$_1$, Ar$_2$, Ar$_3$, and Ar$_4$ is a monovalent group represented by a following structural formula (B) or has the monovalent group as a substituent;

[Chem. 2]

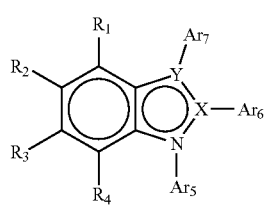
(B)

where, in the structural formula (B), $R_1$, $R_2$, $R_3$, and $R_4$ may be the same or different from each other, be a linking group, a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_1$, $R_2$, $R_3$, and $R_4$ may be bonded to each other to form a ring via a single bond, a substituted or unsubstituted methylene group, an oxygen atom, a sulfur atom, or N—$Ar_8$, where $Ar_8$ represents a substituted or unsubstituted aromatic hydrocarbon group, a substituted or unsubstituted aromatic heterocyclic group, or a substituted or unsubstituted condensed polycyclic aromatic group, X represents a carbon atom or a nitrogen atom, Y represents a carbon atom, an oxygen atom, a sulfur atom, or a nitrogen atom, $Ar_5$ represents a linking group, a substituted or unsubstituted aromatic hydrocarbon group, a substituted or unsubstituted aromatic heterocyclic group, or a substituted or unsubstituted condensed polycyclic aromatic group, wherein $Ar_6$ and $Ar_7$ may be the same or different from each other, be a linking group, a substituted or unsubstituted aromatic hydrocarbon group, a substituted or unsubstituted aromatic heterocyclic group, or a substituted or unsubstituted condensed polycyclic aromatic group, wherein Y does not have $Ar_7$ in the case that Y is an oxygen atom or a sulfur atom, wherein any one of $Ar_5$, $Ar_6$, and $Ar_7$ is a linking group or a substituent in the case that X and Y are each a nitrogen atom, wherein X does not have $Ar_6$ in the case that X is a nitrogen atom and Y is a carbon atom, wherein $Ar_8$ represents a substituted or unsubstituted aromatic hydrocarbon group, a substituted or unsubstituted aromatic heterocyclic group, or a substituted or unsubstituted condensed polycyclic aromatic group, wherein only one of $R_1$, $R_2$, $R_3$, $R_4$, $Ar_5$, $Ar_6$, and $Ar_7$ is a linking group, and a case that X is a nitrogen atom and Y is an oxygen atom or sulfur atom is excluded; and wherein the electron transport layer includes a following compound (3-4):

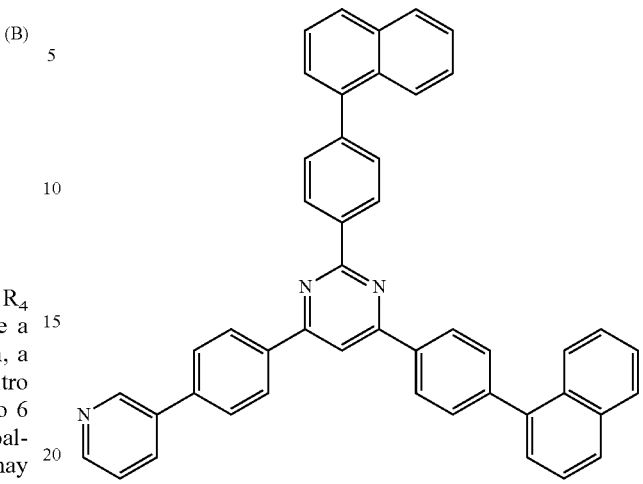
(3-4)

2. The organic electroluminescence device according to claim 1, wherein
the material of the capping layer has an extinction coefficient of not less than 0.1 at wavelengths of from 410 nm to 430 nm.

3. The organic electroluminescence device according to claim 1, wherein
the structural formula (B) is a monovalent group represented by a following structural formula (B-1):

[Chem. 3]

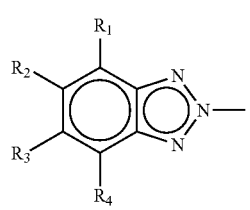
(B-1)

where, in the structural formula (B-1), $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_1$, $R_2$, $R_3$, and $R_4$ may be bonded to each other to form a ring via a single bond, a substituted or unsubstituted methylene group, an oxygen atom, a sulfur atom, or N—$Ar_8$, wherein $Ar_8$ represents a substituted or unsubstituted aromatic hydrocarbon group, a substituted or unsubstituted aromatic heterocyclic group, or a substituted or unsubstituted condensed polycyclic aromatic group.

4. The organic electroluminescence device according to claim 1, wherein
the structural formula (B) is a monovalent group represented by a following structural formula (B-2):

[Chem. 4]

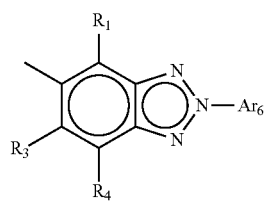

(B-2)

where, in the structural formula (B-2), $R_1$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_3$ and $R_4$ may be bonded to each other to form a ring via a single bond, a substituted or unsubstituted methylene group, an oxygen atom, a sulfur atom, or N—$Ar_8$, wherein $Ar_6$ and $Ar_8$ may be the same or different from each other and each represent a substituted or unsubstituted aromatic hydrocarbon group, a substituted or unsubstituted aromatic heterocyclic group, or a substituted or unsubstituted condensed polycyclic aromatic group.

5. The organic electroluminescence device according to claim 1, wherein
the structural formula (B) is a monovalent group represented by a following structural formula (B-3):

[Chem. 5]

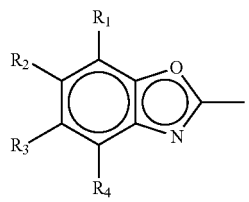

(B-3)

where, in the structural formula (B-3), $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_1$, $R_2$, $R_3$, and $R_4$ may be bonded to each other to form a ring via a single bond, a substituted or unsubstituted methylene group, an oxygen atom, a sulfur atom, or N—$Ar_8$, wherein $Ar_8$ represents a substituted or unsubstituted aromatic hydrocarbon group, a substituted or unsubstituted aromatic heterocyclic group, or a substituted or unsubstituted condensed polycyclic aromatic group.

6. The organic electroluminescence device according to claim 1, wherein
the structural formula (B) is a monovalent group represented by a following structural formula (B-4):

[Chem. 6]

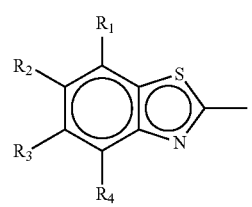

(B-4)

where, in the structural formula (B-4), $R_1$, $R_2$, $R_3$, and $R_4$ may be the same or different from each other, be a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_1$, $R_2$, $R_3$, and $R_4$ may be bonded to each other to form a ring via a single bond, a substituted or unsubstituted methylene group, an oxygen atom, a sulfur atom, or N—$Ar_8$, wherein $Ar_8$ represents a substituted or unsubstituted aromatic hydrocarbon group, a substituted or unsubstituted aromatic heterocyclic group, or a substituted or unsubstituted condensed polycyclic aromatic group.

7. The organic electroluminescence device according to claim 1, wherein
the structural formula (B) is a monovalent group represented by a following structural formula (B'):

[Chem. 7]

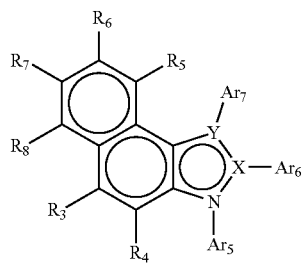

(B')

where, in the structural formula (B'), $R_3$, $R_4$, $R_5$, $R_6$, $R_7$, and $R_8$ may be the same or different from each other, be a linking group, a hydrogen atom, a deuterium atom, a fluorine atom, a chlorine atom, a cyano group, a nitro group, a linear or branched alkyl group having 1 to 6 carbon atoms, which may have a substituent, a cycloalkyl group having 5 to 10 carbon atoms, which may have a substituent, a linear or branched alkenyl group having 2 to 6 carbon atoms, which may have a substituent, a linear or branched alkyloxy group having 1 to 6 carbon atoms, which may have a substituent, a cycloalkyloxy group having 5 to 10 carbon atoms, which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group, wherein $R_3$, $R_4$, $R_5$, $R_6$, $R_7$, and $R_8$ may be bonded to each other to form a ring via a single bond, a substituted or unsubstituted methylene group, an oxygen atom, a sulfur atom, or N—$Ar_8$, where X represents a carbon atom or a nitrogen atom, Y represents a carbon atom, an oxygen atom, a sulfur atom, or a nitrogen atom, wherein $Ar_5$ represents a linking group, a substituted or unsubstituted aromatic hydrocarbon group, a substituted or unsubstituted aromatic heterocyclic group, or a substituted or unsubstituted condensed polycyclic aromatic group, wherein $Ar_6$ and $Ar_7$ may be the same or different from each other and each represent a linking group, a substituted or unsubstituted aromatic hydrocarbon group, a substituted or unsubstituted aromatic heterocyclic group, or a substituted or unsubstituted condensed polycyclic aromatic group, wherein Y does not have $Ar_7$ in the case that Y is an oxygen atom or a sulfur atom, wherein any one of $Ar_5$, $Ar_6$, and $Ar_7$ is a linking group or a substituent in the case that X and Y are each a nitrogen atom, wherein X does not have $Ar_6$ in the case that X is a nitrogen atom and Y is a carbon atom, wherein $Ar_8$ represents a substituted or unsubstituted aromatic hydrocarbon group, a substituted or unsubstituted aromatic heterocyclic group, or a substituted or unsubstituted condensed polycyclic aromatic group, wherein only one of $R_3$, $R_4$, $R_5$, $R_6$, $R_7$, $R_8$, $Ar_5$, $Ar_6$, and $Ar_7$ is a linking group, and a case that X is a nitrogen atom and Y is an oxygen atom or sulfur atom is excluded.

8. The organic electroluminescence device according to claim 1, wherein
n is 0 in the general formula (1).

9. The organic electroluminescence device according to claim 1, wherein
n is 1 in the general formula (1).

10. The organic electroluminescence device according to claim 1, wherein
n is 2 in the general formula (1).

11. The organic electroluminescence device according to claim 1, wherein
any two of $Ar_1$, $Ar_2$, $Ar_3$, and $Ar_4$ are each a monovalent group represented by the structural formula (B) or each has the monovalent group as a substituent in the general formula (1).

12. The organic electroluminescence device according to claim 1, wherein
$Ar_1$ and $Ar_4$ are each a monovalent group represented by the structural formula (B) or each has the monovalent group as a substituent in the general formula (1).

13. The organic electroluminescence device according to claim 1, wherein
the capping layer has a thickness in the range of 30 nm to 120 nm.

14. The organic electroluminescence device according to claim 1, wherein
the capping layer has a refractive index of not less than 1.85 in the wavelength range of 400 nm to 750 nm of light transmitted through the capping layer.

15. A method of using a compound represented by the general formula (1) as a capping layer of an organic electroluminescence device.

* * * * *